US010398510B2

(12) United States Patent
Goto

(10) Patent No.: US 10,398,510 B2
(45) Date of Patent: Sep. 3, 2019

(54) MANUFACTURING METHOD OF BONE CUTTING ASSIST DEVICE, NON-TRANSITORY COMPUTER-READABLE RECORDING MEDIUM HAVING PROGRAM FOR MANUFACTURING BONE CUTTING ASSIST DEVICE RECORDED THEREON, AND BONE CUTTING ASSIST DEVICE

(71) Applicant: Makoto Goto, Nishinomiya (JP)

(72) Inventor: Makoto Goto, Nishinomiya (JP)

( * ) Notice: Subject to any disclaimer, the term of this patent is extended or adjusted under 35 U.S.C. 154(b) by 423 days.

(21) Appl. No.: 15/035,915

(22) PCT Filed: Aug. 1, 2014

(86) PCT No.: PCT/JP2014/070330
§ 371 (c)(1),
(2) Date: May 11, 2016

(87) PCT Pub. No.: WO2015/072187
PCT Pub. Date: May 21, 2015

(65) Prior Publication Data
US 2016/0287335 A1 Oct. 6, 2016

(30) Foreign Application Priority Data
Nov. 12, 2013 (JP) .................. 2013-234450

(51) Int. Cl.
| A61B 17/15 | (2006.01) |
| A61B 17/17 | (2006.01) |
| A61B 34/10 | (2016.01) |
| B33Y 10/00 | (2015.01) |
| B33Y 50/02 | (2015.01) |
| B33Y 80/00 | (2015.01) |
| A61B 17/80 | (2006.01) |
| G05B 19/4099 | (2006.01) |
| A61B 17/00 | (2006.01) |

(52) U.S. Cl.
CPC .............. *A61B 34/10* (2016.02); *A61B 17/15* (2013.01); *A61B 17/17* (2013.01); *A61B 17/80* (2013.01);
(Continued)

(58) Field of Classification Search
CPC .......... A61B 2017/00526; A61B 17/15; A61B 17/151; A61B 17/17; A61B 17/1728; A61B 34/10; A61B 2034/102; A61B 2034/108
See application file for complete search history.

(56) References Cited

U.S. PATENT DOCUMENTS 6,711,432 B1   3/2004 Krause et al.
7,603,192 B2  10/2009 Martin et al.
(Continued)

FOREIGN PATENT DOCUMENTS

EP       1624812 A1    2/2006
JP   2006-519636 A    8/2006
(Continued)

OTHER PUBLICATIONS

Extended European Search Report dated Jul. 18, 2017, mailed in the corresponding European Patent Application No. 14862601.3.
(Continued)

*Primary Examiner* — Nicholas W Woodall
(74) *Attorney, Agent, or Firm* — IP Business Solutions, LLC

(57) ABSTRACT

A manufacturing method of a bone cutting assist device includes generating a bone cutting assist device model representing the bone cutting assist device including a fitting surface that fits a surface of a bone model, a cutting slit that guides a cutting jig, a first guide hole for inserting a first rod model, and second guide holes for inserting second rod models. The manufacturing method also includes outputting three-dimensional manufacturing data representing the generated bone cutting assist device model, and manufacturing the bone cutting assist device according to the outputted three-dimensional manufacturing data.

12 Claims, 24 Drawing Sheets

(52) U.S. Cl.
CPC .............. *B33Y 10/00* (2014.12); *B33Y 50/02* (2014.12); *B33Y 80/00* (2014.12); *G05B 19/4099* (2013.01); *A61B 2017/00526* (2013.01); *A61B 2034/108* (2016.02); *G05B 2219/35134* (2013.01); *G05B 2219/49007* (2013.01)

(56) References Cited

U.S. PATENT DOCUMENTS

| | | | |
|---|---|---|---|
| 2007/0173815 A1* | 7/2007 | Murase | A61B 17/15 606/53 |
| 2008/0195240 A1 | 8/2008 | Martin et al. | |
| 2012/0253410 A1 | 10/2012 | Taylor et al. | |

FOREIGN PATENT DOCUMENTS

| | | |
|---|---|---|
| JP | 2011-172977 A | 9/2011 |
| WO | WO2004071309 A1 | 8/2004 |
| WO | 2012122317 A2 | 9/2012 |
| WO | 2013053614 A1 | 4/2013 |
| WO | WO2013156545 A1 | 10/2013 |

OTHER PUBLICATIONS

International Search Report dated Nov. 18, 2014 issued in corresponding PCT/JP2014/070330 application (pp. 1-3).

\* cited by examiner

MANUFACTURING METHOD OF BONE CUTTING ASSIST DEVICE, NON-TRANSITORY COMPUTER-READABLE RECORDING MEDIUM HAVING PROGRAM FOR MANUFACTURING BONE CUTTING ASSIST DEVICE RECORDED THEREON, AND BONE CUTTING ASSIST DEVICE

TECHNICAL FIELD

The present invention relates to a bone cutting assist device to be used for cutting a bone deformed owing to bone fracture or the like, a manufacturing method of the bone cutting assist device, and a manufacturing program of the bone cutting assist device.

BACKGROUND ART

To treat bone fracture or deformation in a human body, two-dimensional fluoroscopic images obtained with X-ray, computed tomography (CT), or perspective images are utilized for making a preoperative planning and performing a bone cutting or correcting operation. However, since the actual deformation of the human bone is three-dimensional, it is difficult to accurately simulate the bone cutting or correcting operation according to the actual situation, before the operation. In the actual practice of the operation, therefore, the bone may be cut at a position deviated from the target position, or the correction may result insufficient. As remedy for such drawback, a bone cutting assist device to be used for operations to treat bone fracture or deformation has been proposed. The assist device is configured to move divided bone pieces obtained by cutting a bone deformed into an abnormal condition to positions for forming the bone of the normal condition. With the device according to Patent Literature (PTL) 1, for example, even an inexperienced surgeon can easily move the divided bone pieces to the target position for the correction, after cutting the bone of an abnormal condition for performing the corrective operation.

CITATION LIST

Patent Literature

PTL 1: Japanese Unexamined Patent Application Publication No. 2011-172977

SUMMARY OF INVENTION

The bone cutting assist device according to PTL 1 has to be attached, when cutting the bone, to the surface of the bone to be treated at a position corresponding to a cutting cross-section. The bone cutting assist device includes a fitting surface to be fitted on the surface of the bone to be treated, so that the bone cutting assist device is attached to the position corresponding to the cutting cross-section, by attaching the bone cutting assist device such that the fitting surface is located so as to fit the shape of the bone surface. However, in the actual site where the surgeon practically performs the operation for treating the bone of a human body, the condition of the bone is often different from what has been predicted, and the positioning of the bone cutting assist device utilizing the fitting surface may not always be accurately carried out. Therefore, it is desired that the positioning with respect to the bone to be treated can be performed with higher accuracy, so that a more appropriate treatment can be performed for the bone to be treated.

The present invention has been accomplished in view of the foregoing problem, and provides a technique for facilitating correction of a bone deformed into an abnormal condition to the normal condition with higher accuracy than ever, without depending on a special technique or the experience of the surgeon.

In an aspect, the present invention provides a manufacturing method of a bone cutting assist device used for cutting a bone deformed into an abnormal condition. The method includes acquiring three-dimensional data of a bone to be treated and generating a three-dimensional bone model representing the bone to be treated, on a basis of the acquired three-dimensional data, generating bone piece models divided by cutting the bone model along a cutting cross-section for correction defined with respect to the bone model, the bone piece models being movable or rotatable to a target correction position approximate to a target bone model representing a correction goal of the bone to be treated, calculating a position of a first rod model attached to a predetermined feature point of the bone model, calculating, on a basis of a position of a second rod model attached to each of the bone piece models assumed to be located at the target correction position, a position of the second rod model on an assumption that the bone piece models are located at a position corresponding to the bone model, generating a bone cutting assist device model representing a bone cutting assist device including a fitting surface to be fitted to a surface of the bone model, a cutting slit formed at a position corresponding to the cutting cross-section, to guide a cutting jig toward the cutting cross-section, a first guide hole formed at the calculated position of the first rod model, so as to allow the first rod model to be inserted, and a second guide hole formed at the calculated position of the second rod model, so as to allow the second rod model to be inserted, outputting three-dimensional manufacturing data representing the generated bone cutting assist device model, and manufacturing the bone cutting assist device according to the outputted three-dimensional manufacturing data.

In another aspect, the present invention provides a manufacturing program of a bone cutting assist device. The program includes causing a computer to act as a bone model generation unit that acquires three-dimensional data of a bone to be treated and generates a three-dimensional bone model representing the bone to be treated, on a basis of the acquired three-dimensional data, a bone piece model generation unit that generates bone piece models divided by cutting the bone model along a cutting cross-section for correction defined with respect to the bone model, the bone piece models being movable or rotatable to a target correction position approximate to a target bone model representing a correction goal of the bone to be treated, a first rod model position calculation unit that calculates a position of a first rod model attached to a predetermined feature point of the bone model, a second rod model position calculation unit that calculates, on a basis of a position of a second rod model attached to each of the bone piece models assumed to be located at the target correction position, a position of the second rod model on an assumption that the bone piece models are located at a position corresponding to the bone model, a bone cutting assist device model generation unit that generates a bone cutting assist device model representing a bone cutting assist device including a fitting surface to be fitted to a surface of the bone model, a cutting slit formed at a position corresponding to the cutting cross-section, to guide a cutting jig toward the cutting cross-section, a first guide hole formed at the calculated position of the first rod model, so as to allow the first rod model to be inserted, and a second guide hole formed at the calculated position of the second rod model, so as to allow the second rod model to be inserted, and a manufacturing data output unit that outputs three-dimensional manufacturing data representing the generated bone cutting assist device model.

In still another aspect, the present invention provides a bone cutting assist device used for cutting and dividing a bone deformed into an abnormal condition. The bone cutting assist device includes a cutting slit formed at a position corresponding to a cutting cross-section along which the bone is to be cut, and configured to guide a cutting jig toward the cutting cross-section when the bone cutting assist device is in contact with a surface of the bone, a first guide hole that guides a first rod to be inserted into the bone to a predetermined feature point of the bone, when the bone cutting assist device is in contact with the surface of the bone, and a second guide hole that guides a second rod to be inserted into the bone to the bone, when the bone cutting assist device is in contact with the surface of the bone.

In still another aspect, the present invention provides a bone cutting assist device used for cutting a bone deformed into an abnormal condition into bone pieces, along a predetermined cutting cross-section. The bone cutting assist device includes a fitting surface formed at a position to oppose the bone to be corrected, so as to fit to a surface of the bone, a cutting slit formed at a position corresponding to the cutting cross-section, to guide a cutting jig toward the cutting cross-section, when the fitting surface is fitted to the surface of the bone, a first guide hole that guides a first rod to be inserted into the bone to a predetermined feature point of the bone when the fitting surface is fitted to the surface of the bone, and a second guide hole that guides, when the fitting surface is fitted to the surface of the bone, a second rod to be inserted into the bone, such that the second rods thrust into the bone pieces assume a predetermined positional relationship therebetween, after the bone pieces divided along the cutting cross-section are corrected to a positional relationship in the normal condition.

With the bone cutting assist device configured as above, an operation for correcting a bone deformed into an abnormal condition to a normal condition can be easily performed with higher accuracy than ever, without depending on a special technique or the experience of the surgeon.

DESCRIPTION OF EMBODIMENT

Hereafter, a manufacturing method and a manufacturing program of a bone cutting assist device according to an embodiment of the present invention, as well as the bone cutting assist device, will be described with reference to the drawings.

Figure 1:
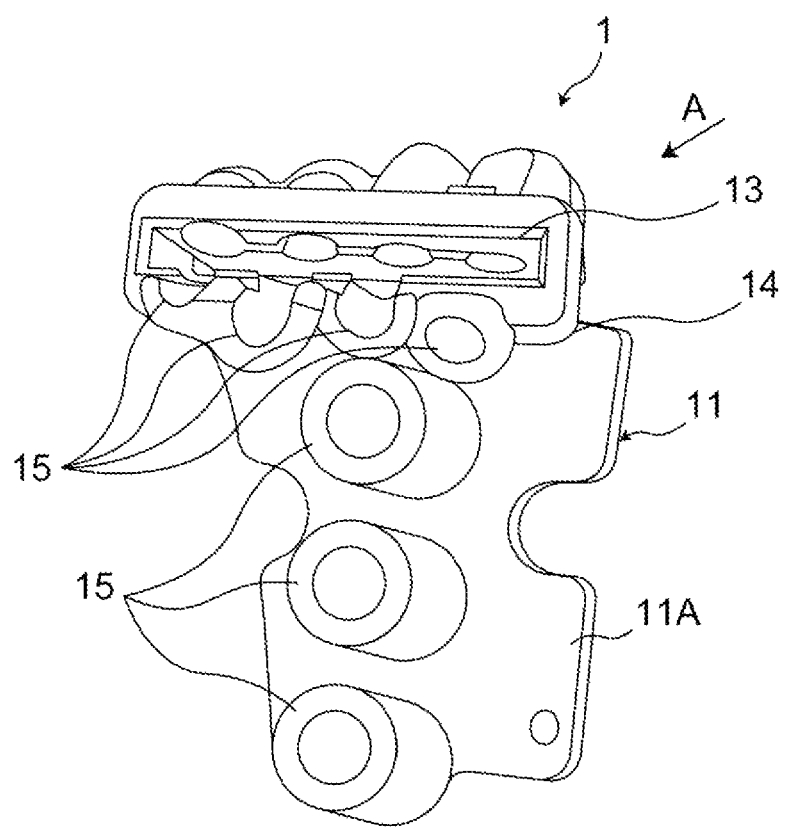
FIG. 1 is a perspective view showing a bone cutting assist device according to an embodiment of the present invention.
Figure 2:
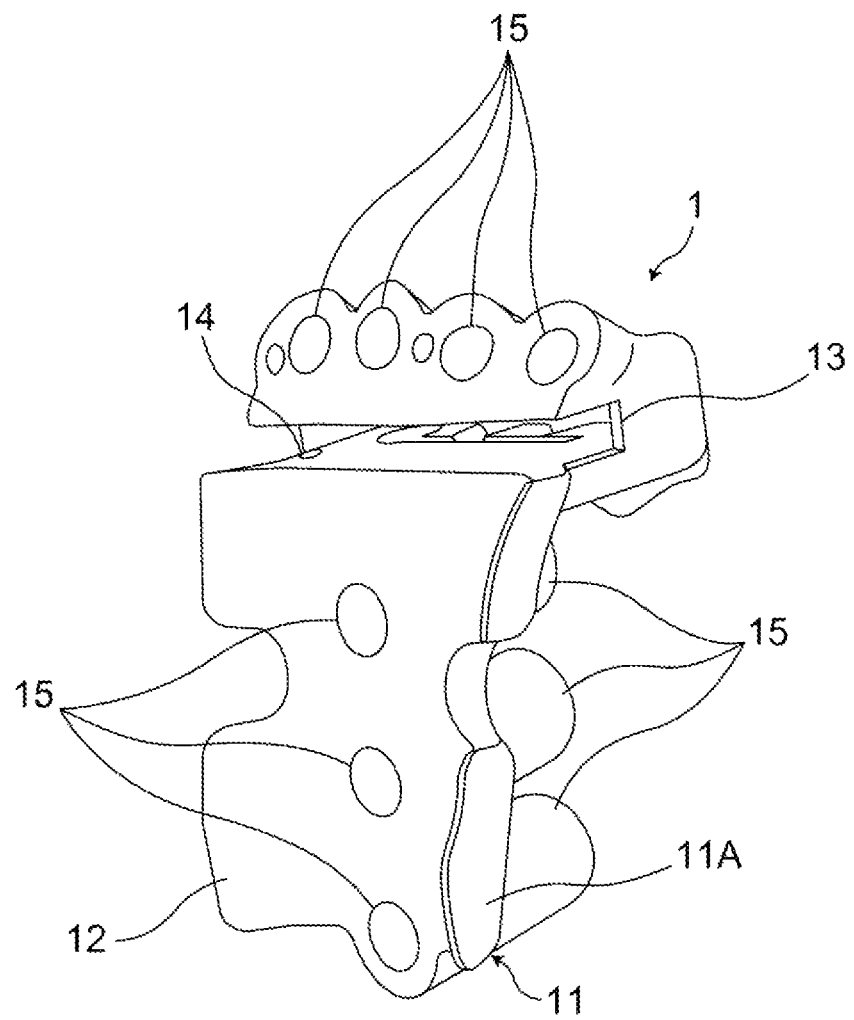
FIG. 2 is a perspective view showing the bone cutting assist device of FIG. 1, seen from a direction indicated by an arrow A in FIG. 1.
Figure 3:
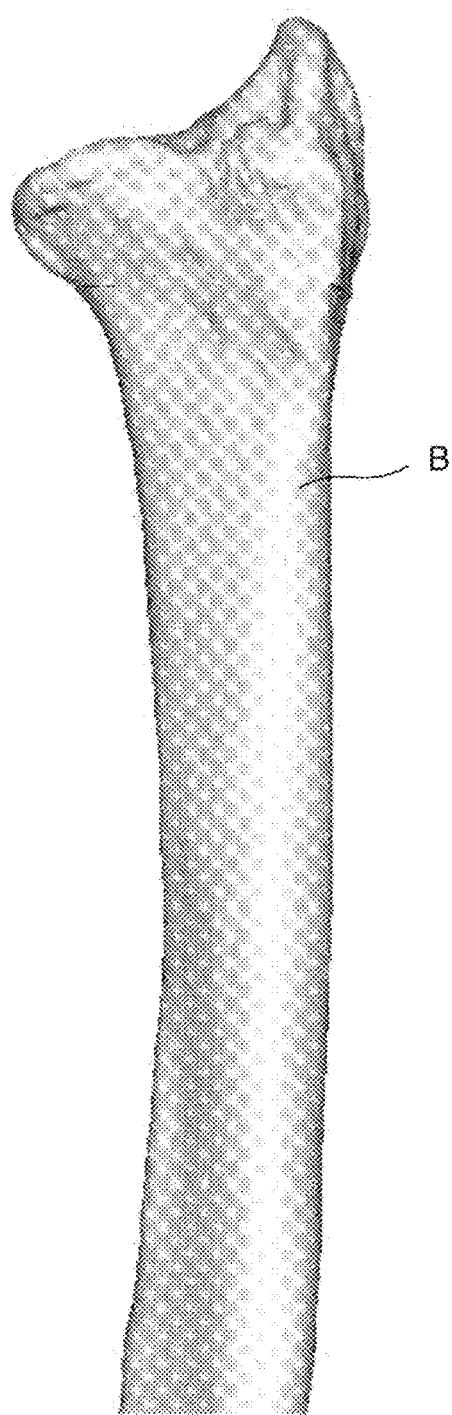
FIG. 3 is a perspective view showing a bone to be treated.
Figure 4:
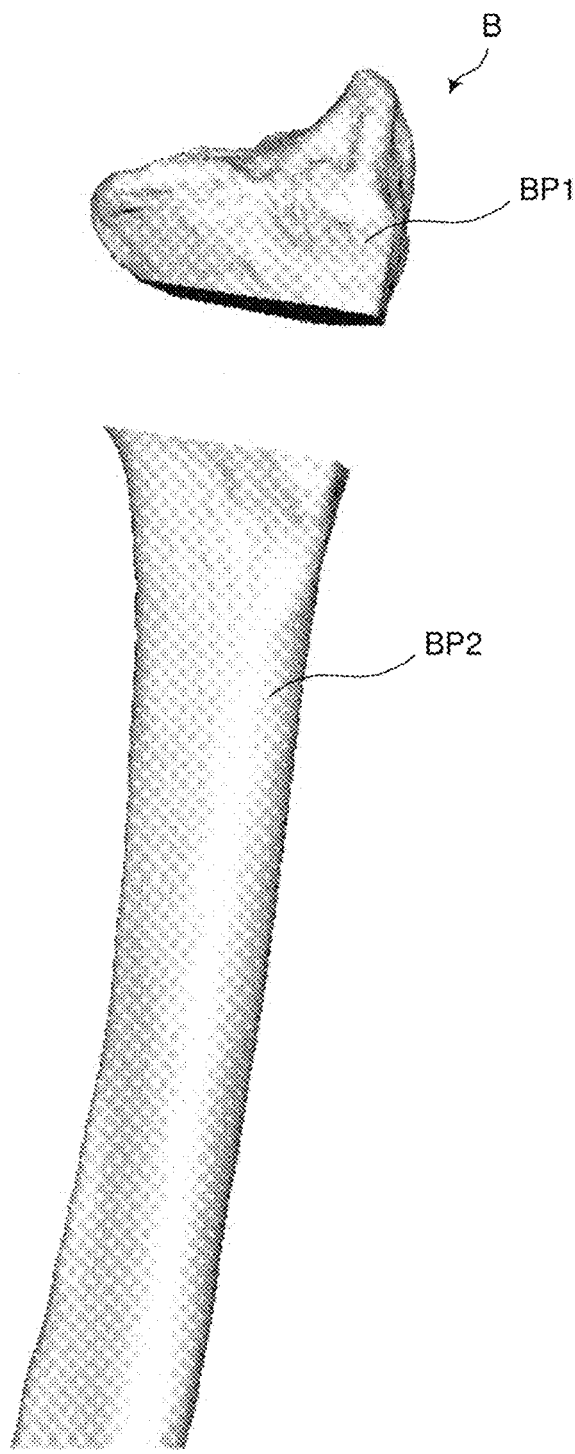
FIG. 4 is a perspective view of the bone to be treated, cut into divided bone pieces.

FIG. 1 is a perspective view showing the bone cutting assist device according to the embodiment of the present invention. FIG. 2 is a perspective view showing the bone cutting assist device of FIG. 1, seen from a direction indicated by an arrow A in FIG. 1. FIG. 3 is a perspective view showing a bone to be treated. FIG. 4 is a perspective view of the bone to be treated, cut into divided bone pieces.

The bone cutting assist device 1 is configured to cut a bone B deformed into an abnormal condition along a predetermined cutting cross-section, thereby dividing the bone B. The bone B is divided into bone pieces BP1, BP2, upon being cut by the bone cutting assist device 1. Either or both of the bone pieces BP1, BP2 are moved and/or rotated (hereinafter simply expressed as moved) by a surgeon to a target correction position representing a normal condition. The bone cutting assist device 1 is manufactured, for example, through a rapid prototyping method such as optical modelling, on the basis of three-dimensional model data generated and outputted through a bone cutting assist device manufacturing program as will be subsequently described. The bone cutting assist device 1 may be formed of a resin, for example.

The bone cutting assist device 1 includes a main body 11, a fitting surface 12, a cutting slit 13, a first guide hole 14, and second guide holes 15.

The main body 11 is formed in a shape that fits the shape of the surface of a bone to be treated. The fitting surface 12 is formed on a side face of the main body 11, at a position opposing the bone B to be treated. The fitting surface 12 is formed in a shape that fits the surface shape of the bone B. The fitting surface 12 is formed on the basis of three-dimensional data of the bone B obtained, for example, through a CT process.

To acquire the three-dimensional data of the bone B, any available device may be employed provided that the three-dimensional model of the object can be obtained. Examples of applicable devices include, but are not limited to, a CCD camera, an optical camera, X-ray photography, CT, and magnet resonance imaging (MRI).

The cutting slit 13 serves to guide a cutting jig to the predetermined cutting cross-section, when the bone cutting assist device 1 is attached to the bone B with the fitting surface 12 fitted to the surface of the bone. The cutting slit 13 is formed on a side face 11A of the main body 11. The cutting jig may be, for example, an electric saw. The cutting cross-section may be a flat plane for example, which can be defined by a position on the surface of the bone B and an angle with respect to the surface of the bone B. The cutting cross-section is defined by the surgeon in advance of the operation of the bone B to be treated. The cutting slit 13 is formed in a shape that allows, when the electric saw is employed as the cutting jig, the saw blade to be inserted, so as to guide the saw blade to the cutting cross-section determined by the position and angle with respect to the bone B.

The first guide hole 14 is formed as an elongate slit so as to guide a first rod (illustrated in the drawings to be subsequently referred to) to inserted in the bone B to a feature point on the bone B. In this embodiment, the first rod is formed of a bar-shaped material. The first rod may be formed of a metal, with a pointed tip portion that enables insertion into the bone. The first rod has the same or a slightly smaller diameter than the first guide hole 14.

The first guide hole 14 has the same or a slightly larger diameter than the first rod, so as to allow the first rod to be inserted therethrough. The first guide hole 14 has a certain width in a direction in which the first rod is inserted, to support the inserted first rod.

The feature point refers to a part of the bone B specified in advance by the surgeon. When the bone B to be treated has a shape shown in FIG. 3 for example, the surgeon determines before the operation a part of the bone B where the first rod is to be inserted, as the feature point. Preferred feature points include, for example in an upper limb region, a tip portion of a styloid process, and epicondyle of humerus. The position and angle of the first rod with respect to the bone B, at which the first rod is to be thrust into the bone B, is determined on the premise that the first rod passes through the feature point. The first guide hole 14 is formed in the shape that guides the first rod at such a position and angle with respect to the bone B.

Thus, the first guide hole 14 is formed such that the elongate slit extends along the passage of the first rod thrust into the bone B at the mentioned position and angle. The position and angle of the first guide hole 14 is determined so as to allow the first rod to pass through the feature point upon being inserted through the first guide hole 14 and thrust into the bone B.

The second guide hole 15 is formed in a shape that guides a second rod (illustrated in the drawings to be subsequently referred to) to be inserted in the bone B to a predetermined thrusting position, when the bone cutting assist device 1 is attached to the bone B with the fitting surface 12 fitted to the surface of the bone. In this embodiment, the second rod is formed in the same shape as the first rod. The second rod has the same or a slightly smaller diameter than the second guide hole 15. The second guide hole 15 is formed so as to extend along the passage of the second rod thrust into the bone B.

The thrusting positions of the second rod are determine such that, when the bone pieces BP1, BP2 produced by cutting the bone B to be treated along the cutting cross-section are moved to the target correction position to form the bone of the normal condition, the second rods thrust into the bone pieces BP1, BP2 assume a predetermined positional relationship therebetween.

In this embodiment, four second rods are thrust into the bone piece BP1, and three second rods are thrust into the bone piece BP2. Accordingly, the main body 11 includes four second guide holes 15 for the bone piece BP1, and three second guide holes 15 for the bone piece BP2. However, the number of second guide holes 15 formed for the bone pieces BP1, BP2 is not specifically limited.

Figure 5:
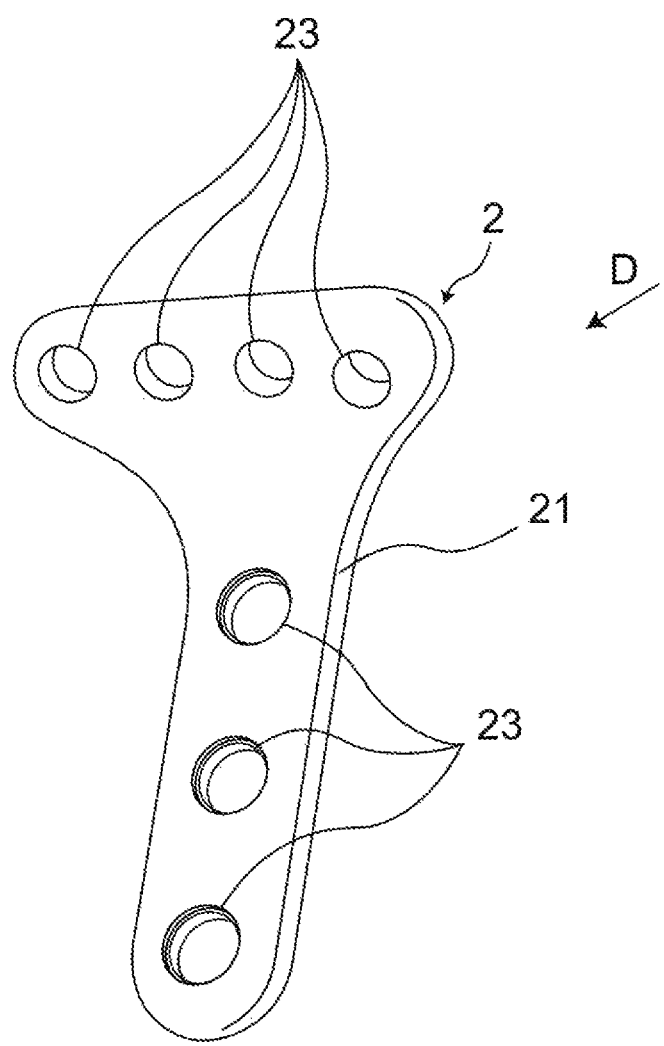
FIG. 5 is a perspective view showing a block.
Figure 6:
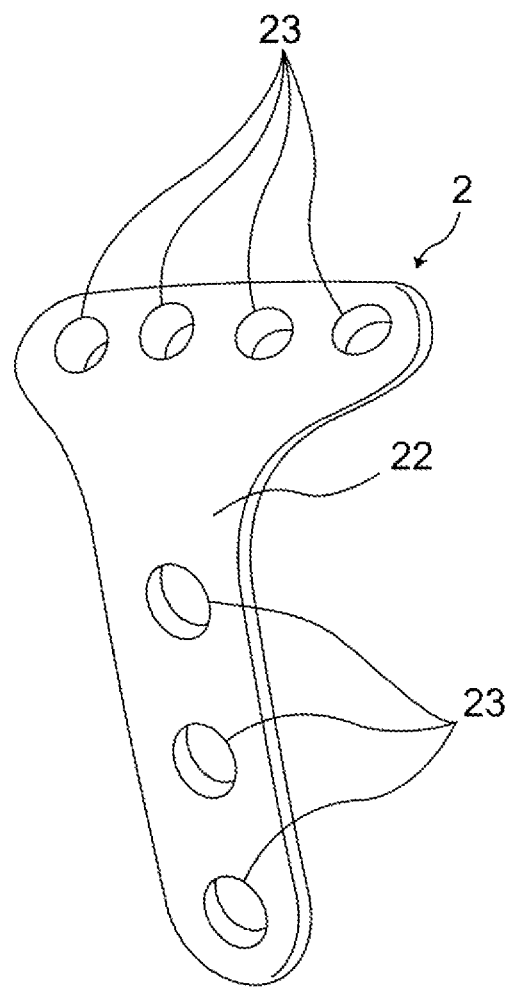
FIG. 6 is a perspective view showing the block of FIG. 5, seen from a direction indicated by an arrow D in FIG. 5.

Hereunder, a block 2 will be described. FIG. 5 is a perspective view showing the block 2. FIG. 6 is a perspective view showing the block 2 of FIG. 5, seen from a direction indicated by an arrow D in FIG. 5.

The block 2 is applied to the bone pieces BP1, BP2 moved to the target correction position. The block 2 includes a main body 21, a fitting surface 22, and insertion holes 23. The block 2 is, for example, formed of a metal.

The main body 21 is formed in a shape that fits the surface of the corrected bone constituted of the bone pieces BP1, BP2 located at the target correction position. The fitting surface 22 is formed on a side face of the main body 21, at a position to oppose the corrected bone. The fitting surface 22 is formed in the shape that fits the surface shape of the corrected bone calculated on the basis of the three-dimensional data of the bone B before the correction.

The insertion holes 23 are formed at positions respectively corresponding to second rod models thrust into the bone pieces BP1, BP2 when the block 2 is applied to the corrected bone (constituted of the bone pieces BP1, BP2) with the fitting surface 22 fitted to the surface shape thereof. The insertion hole 23 has the same or a slightly larger diameter than the second rod, so as to allow the second rod to be inserted therethrough.

Figure 21:
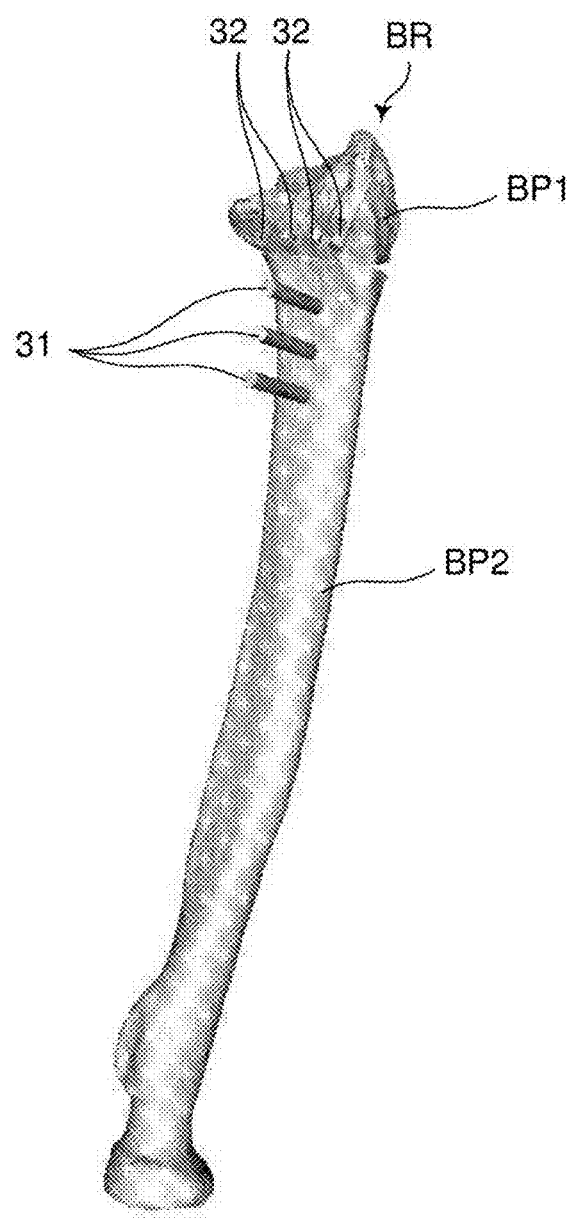
FIG. 21 is a drawing for explaining the operation procedure of the bone to be treated, showing the bone pieces moved to a target correction position.
Figure 22:
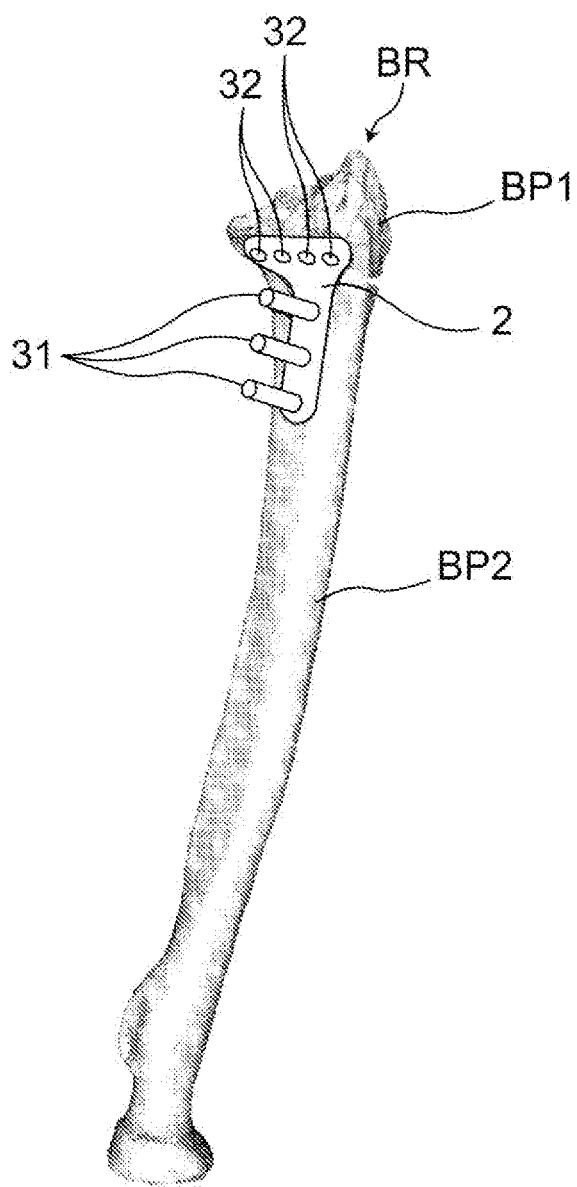
FIG. 22 is a drawing showing the second rods thrust into the bone pieces inserted through insertion holes of the block and applied to the bone pieces.

Accordingly, when all of the second rods thrust into the bone pieces BP1, BP2 can be inserted the respective insertion holes 23, it can be construed that the bone pieces BP1, BP2 have been moved to the target correction position thereby constituting a corrected bone BR (see FIG. 21, FIG. 22). When all of the second rods thrust into the bone pieces BP1, BP2 are unable to be inserted the corresponding insertion holes 23, the bone pieces BP1, BP2 are assumed not to have moved to the position to constitute the corrected bone BR.

In this embodiment, the bone pieces BP1, BP2, each having the second rods thrust thereto, are moved, and when the second rods thrust into one of the bone pieces assume the predetermined positional relationship (details will subsequently follow) with respect to the second rods on the other bone piece, all of the second rods can be inserted through the respective insertion holes 23 of the block 2. When this is achieved, it is construed that the bone pieces BP1, BP2 are in the target correction position with respect to each other.

A bone cutting assist device manufacturing program, employed for manufacturing the bone cutting assist device 1 and the block 2, will now be described hereunder. The bone cutting assist device 1 is manufactured through a rapid prototyping method such as optical modelling, on the basis of three-dimensional model data generated and outputted through the bone cutting assist device manufacturing program. The bone cutting assist device manufacturing program is installed in an information processing apparatus, to be put to use.

Figure 7:
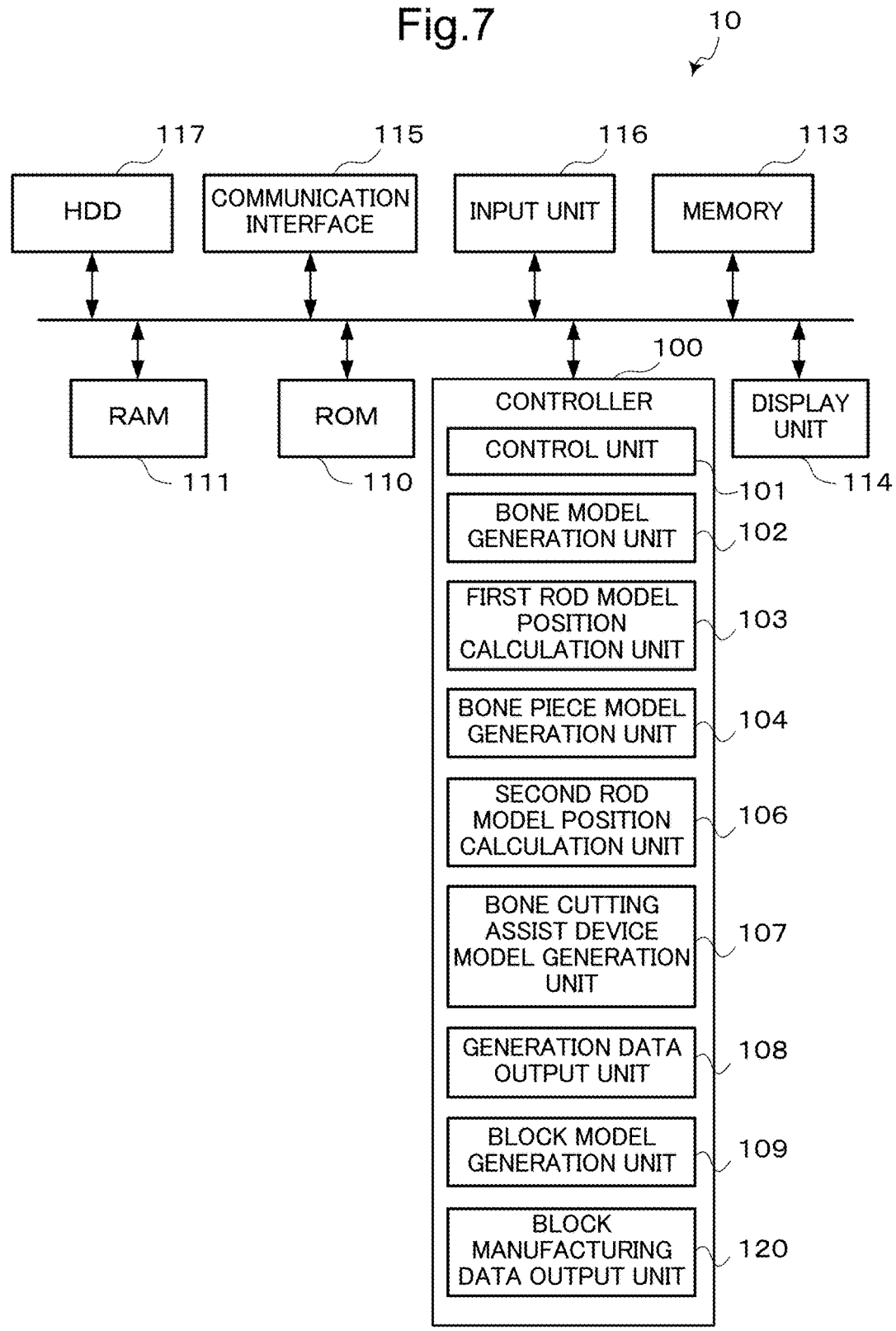
FIG. 7 is a block diagram showing a configuration of an information processing apparatus with a manufacturing program of the bone cutting assist device installed therein.

FIG. 7 is a block diagram showing a configuration of the information processing apparatus with the bone cutting assist device manufacturing program installed therein.

The information processing apparatus 10 includes a controller 100, a ROM 110, a RAM 111, a memory 113, a display unit 114, a communication interface 115, and an input unit 116. These units are configured to transmit and receive data and signals between each other, through a CPU bus.

The controller 100 includes a CPU or the like. The ROM 110 stores operation programs of basic functions of the information processing apparatus 10. The RAM 111 is utilized as operating region for the controller 100.

The memory 113 is a storage medium for storing data such as the three-dimensional model data for manufacturing the bone cutting assist device 1 and the block 2 transmitted from the imaging apparatus.

HDD 117 is a storage region where the bone cutting assist device manufacturing program is installed.

The controller 100 includes a control unit 101, a bone model generation unit 102, a first rod model position calculation unit 103, a bone piece model generation unit 104, a second rod model position calculation unit 106, a bone cutting assist device model generation unit 107, a generation data output unit 108, a block model generation unit 109, and a block manufacturing data output unit 120.

The controller 100 acts, upon operating according to the bone cutting assist device manufacturing program installed in the HDD 117, as the control unit 101, the bone model generation unit 102, the first rod model position calculation unit 103, the bone piece model generation unit 104, the second rod model position calculation unit 106, the bone cutting assist device model generation unit 107, the generation data output unit 108, the block model generation unit 109, and the block manufacturing data output unit 120, and thus includes the mentioned units.

Alternatively, the control unit 101, the bone model generation unit 102, the first rod model position calculation unit 103, the bone piece model generation unit 104, the second rod model position calculation unit 106, the bone cutting assist device model generation unit 107, the generation data output unit 108, the block model generation unit 109, and the block manufacturing data output unit 120 may each be constituted of a hardware circuit, instead of being realized through the operation according to the bone cutting assist device manufacturing program. This also applies to other embodiments, unless otherwise specifically noted.

The control unit 101 controls the overall operation of the information processing apparatus 10, for example the displaying operation of the display unit 114.

The bone model generation unit 102 acquires the stereographic three-dimensional data of the bone B to be treated, from the imaging apparatus such as a CT scanner through the communication interface 115. The bone model generation unit 102 generates a three-dimensional bone model representing the bone B, on the basis of the acquired three-dimensional data. The bone model is a stereographic image represented by computer graphics.

The first rod model position calculation unit 103 calculates the position of a first rod model (position of the bone model) assumed to be thrust into the bone model generated by the bone model generation unit 102 at the feature point. The first rod model refers to the stereographic image representing the shape of the first rod, formed by computer graphics. The three-dimensional data representing the first rod model is possessed by the first rod model position calculation unit 103.

The bone piece model generation unit 104 generates bone piece models by cutting the bone model along a cutting cross-section for correction specified with respect to the bone model. For example, the control unit 101 causes the display unit 114 to display a graphic image representing the bone model and a graphic image representing a plurality of cutting cross-sections aligned in the longitudinal direction of the bone model and each inclined by a certain angle with respect to a longitudinal axis of the bone model. The certain angle is determined according to an instruction of the operator inputted in the input unit 116. The operator designates, out of the plurality of graphic images representing the cutting cross-section, a graphic image representing the cutting cross-section located at the desired position with respect to the bone model, through the input unit 116. When such designation is inputted, the bone piece model generation unit 104 acquires coordinate position information indicating the coordinate position where the cutting cross-section corresponding to the designated graphic image is displayed. The operator determines the cutting cross-section for the bone model, through the mentioned operation, so as to enable each of the bone piece models produced by cutting to move to the target correction position approximate to a target bone model representing the correction goal. The bone piece models have different shapes depending on the position and angle of the cutting cross-section along which the bone is cut.

The control unit 101 causes the bone piece models cut as above to be displayed, and then causes the bone piece models to be displayed, according to the instruction of the operator inputted through the input unit 116, with variation of positions on the graphics. Accordingly, the operator can simulate whether the generated bone piece models can be moved to the target correction position, to thereby select the cutting cross-section at the most appropriate position.

The second rod model position calculation unit 106 acquires the position of the second rod models attached to each of the bone piece models located at the target correction position, and calculates, on the basis of the position of the second rod models, the position of the second rod models with respect to the corresponding bone piece model taken when the bone piece models are moved to the position for constituting the bone model. As in this embodiment, for example, a plurality of second rod models are attached to each of the bone piece models located at the target correction position. Alternatively, a single piece of second rod model may be attached to each bone piece model. In the case where a plurality of second rod models are attached to each bone piece model, the second rod models attached to each bone piece model may be set parallel to each other. The second rod model refers to a stereographic image representing the shape of the second rod created by computer graphics. The three-dimensional data representing the second rod model is possessed by the second rod model position calculation unit 106.

The second rod model position calculation unit 106 further calculates the position of the bone piece models and the corresponding second rod models, taken when the bone piece models located at the target correction position are moved to the position of the bone to be treated (before correction), as second rod model position with respect to the bone piece models. The second rod model position calculation unit 106 calculates the position of the second rod models with respect to the bone piece models in the same manner as calculating the position of the first rod model. In addition, the number of second rod models inserted in each of the bone piece models is not specifically limited.

The bone cutting assist device model generation unit 107 generates a bone cutting assist device model, on the basis of the bone model generated as above, the position of the cutting cross-section determined as above, the calculated position of the first rod model, and the calculated position of the second rod model. The bone cutting assist device model is a three-dimensional image representing the bone cutting assist device 1 by a graphic image. The bone cutting assist device model includes a main body model corresponding to the main body 11 of the bone cutting assist device 1, a fitting surface model corresponding to the fitting surface 12, a cutting slit model corresponding to the cutting slit 13, a first guide hole model representing the first guide hole located at the position of the first rod model so as to allow the first rod model to be inserted therethrough, and second guide hole models representing the respective second guide holes located at the calculated positions of the second rod models to allow the second rod models to be inserted therethrough.

The generation data output unit 108 outputs the three-dimensional data representing the bone cutting assist device model generated by the bone cutting assist device model generation unit 107 as three-dimensional data for manufacturing the bone cutting assist device 1, for example to a USB memory, another information processing apparatus, or an NC machine tool, through the communication interface 115. With the three-dimensional manufacturing data, the bone cutting assist device or a tooling for manufacturing the bone cutting assist device can be fabricated.

The block model generation unit 109 generates a block model representing the block. The block model generation unit 109 generates the block model by forming an insertion hole model corresponding to the insertion hole at the position that enables the second rod model acquired by the second rod model position calculation unit 106 to be inserted, and forming a fitting surface model having a shape that fits the surface shape of each of bone piece model located at the target correction position.

The block manufacturing data output unit 120 outputs the three-dimensional data for manufacturing the block, representing the block model generated by the block model generation unit 109, for example to a USB memory, another information processing apparatus, or an NC machine tool, through the communication interface 115. With the three-dimensional data representing the block model, the block or a tooling for manufacturing the block can be fabricated.

Here, the bone model generation unit 102, the first rod model position calculation unit 103, the bone piece model generation unit 104, the second rod model position calculation unit 106, the bone cutting assist device model generation unit 107, the generation data output unit 108, the block model generation unit 109, and the block manufacturing data output unit 120 of the controller 100, may each be constituted of a hardware circuit, instead of being realized through the operation according to the bone cutting assist device manufacturing program. In addition, it suffices that the controller 100 includes the control unit 101, the block model generation unit 109, and the block manufacturing data output unit 120, in so far as the embodiments described hereunder may require.

The display unit 114 is constituted of a liquid crystal display (LCD) or the like, and displays, under the control of the control unit 101, the aforementioned images, the content of various data, user guides for operating the information processing apparatus 10.

The communication interface 115 includes a USB interface for example, and outputs the bone cutting assist device manufacturing data and the block manufacturing data to, for example, an external memory connected to the information processing apparatus 10, another information processing apparatus, or an NC machine tool. The communication interface 115 also serves as an interface for acquiring the three-dimensional data from the imaging apparatus such as a CT scanner, or the USB memory.

The input unit 116 is constituted of a keyboard and a mouse pointer provided in the information processing apparatus 10 and a touch panel device provided in the display screen of the display unit 114, and used by the operator to input various instructions.

Figure 8:
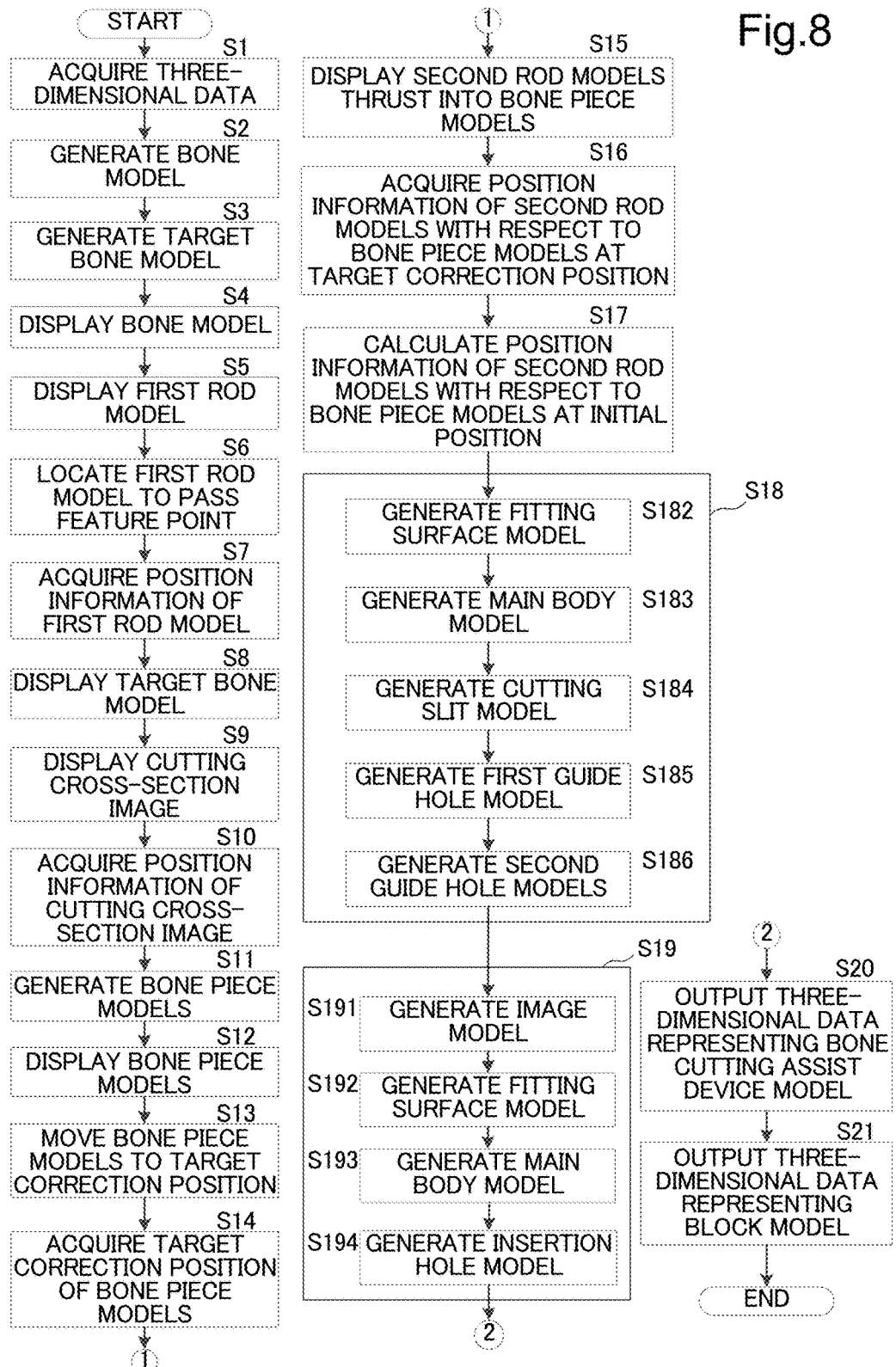
FIG. 8 is a flowchart showing a process performed by the information processing apparatus to generate manufacturing data of the bone cutting assist device.

Hereunder, description will be given on a method of generating the bone cutting assist device manufacturing data to be performed by the information processing apparatus 10 having the bone cutting assist device manufacturing program installed therein. FIG. 8 is a flowchart showing a process performed by the information processing apparatus 10 to generate manufacturing data of the bone cutting assist device.

First, the bone B to be treated in the patient to undergo the corrective operation is shot by an imaging apparatus such as a CT scanner or MRI apparatus. In the case of CT scanning, the imaging apparatus acquires three-dimensional data composed of position information (in an X-direction and Y-direction) on the tomographic image and sets of images shot at different positions in the height direction of the patient (defined as Z-direction), obtained through the imaging. In addition, a normal portion of the patient's bone (for example, a portion of the bone on the side of the tendon, i.e., a portion having the shape to which the bone to be treated is to be corrected) is also shot by the imaging apparatus to acquire the three-dimensional data.

In the information processing apparatus 10, the bone cutting assist device manufacturing program is activated and the controller 100 is made to act as the functional units from the bone model generation unit 102 to the block generation data output unit 120. The operator inputs the three-dimensional data of the bone B to be treated and the three-dimensional data of the normal portion of the bone acquired through the imaging apparatus to the information processing apparatus 10 through the communication interface 115, via a USB memory or USB connection. The bone model generation unit 102 acquires the three-dimensional data from the imaging apparatus through the communication interface 115 (S1).

The bone model generation unit 102 generates a bone model BM representing the bone B, according to the three-dimensional data of the bone B to be treated acquired as above (S2).

The bone model generation unit 102 further generates a target bone model image based on the three-dimensional data of the normal portion of the bone (S3). In the case where the bone model is generated for example from an arm bone as object of correction, such a target bone model image is generated, however when a bone of a different position is the object of correction, the subsequent process may be performed without generating the target bone model.

Figure 9:
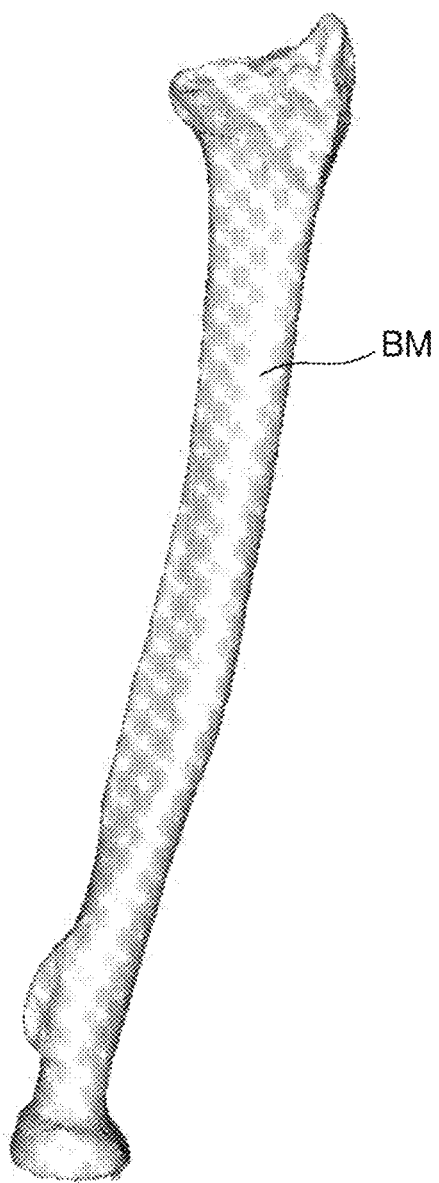
FIG. 9 illustrates an example of a display screen showing a generated bone model.

The control unit 101 of the information processing apparatus 10 causes the display unit 114 to display the bone model BM generated as above (S4). An example of the screen displayed by the display unit 114 is shown in FIG. 9. The control unit 101 causes the bone model BM to be displayed in different angles and positions according to the instruction from the operator inputted through the input unit 116.

Figure 10:
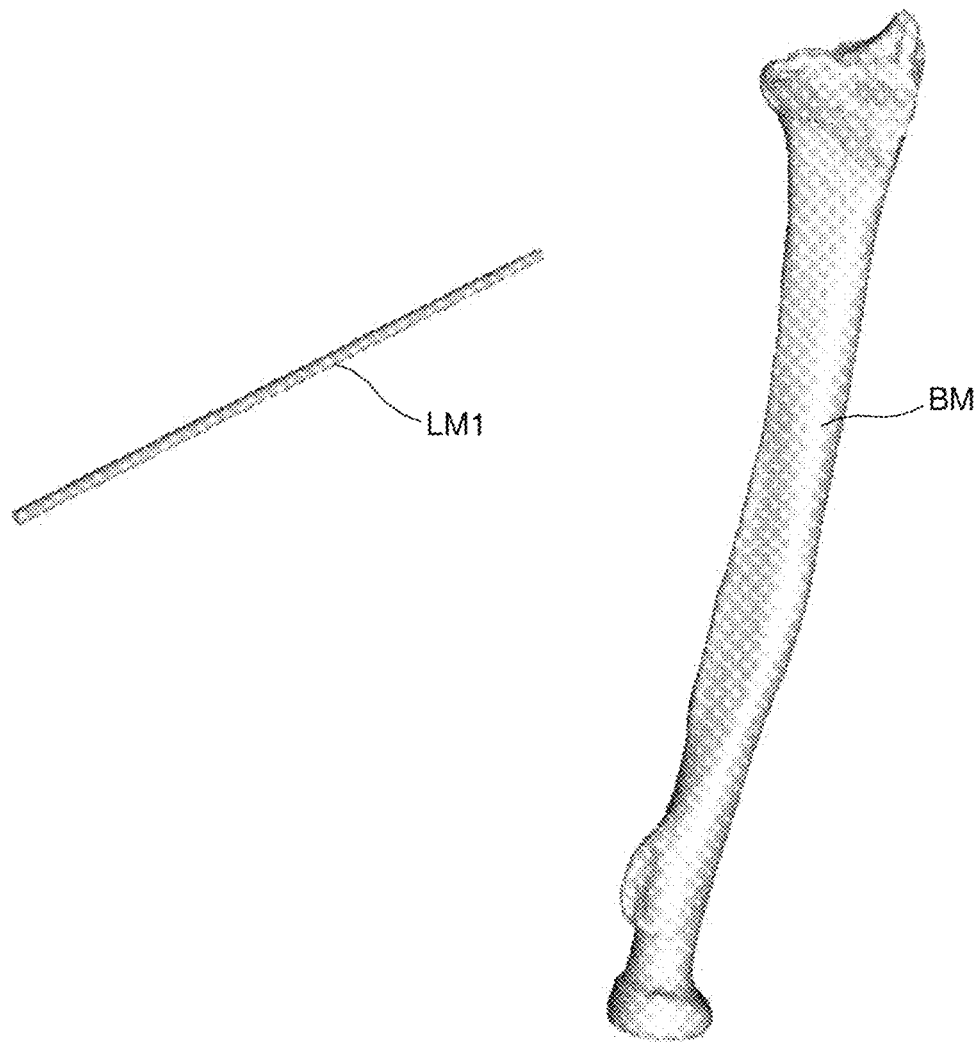
FIG. 10 illustrates an example of the display screen showing a first rod model.

At this point, for example, the first rod model position calculation unit 103 causes the display unit 114 to display an image representing a first rod model LM 1, according to the instruction from the operator inputted through the input unit 116 (S5). An example of the screen displayed by the display unit 114 at this point is shown in FIG. 10.

Figure 11:
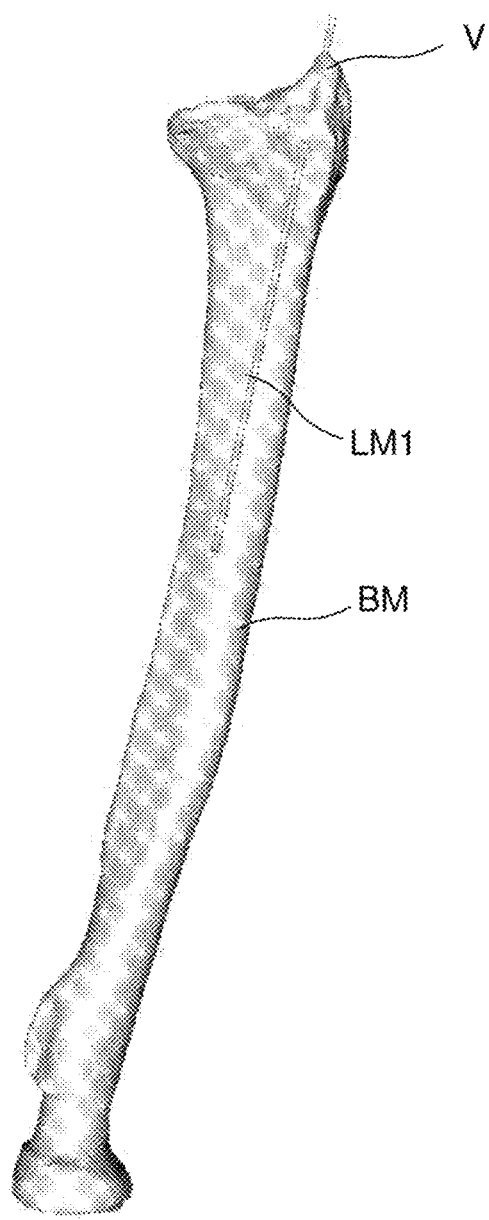
FIG. 11 illustrates an example of the display screen showing the first rod model passing through a feature point of the bone model.

The control unit 101 causes the first rod model LM 1 to be displayed in different positions according to the instruction from the operator inputted through the input unit 116. The operator causes, through the input unit 116, the first rod model LM 1 to be thrust into the bone model BM through a desired position in the bone model BM, for example a feature point V showing a shape that the operator can visually recognize easily in the shape of the bone model BM as shown in FIG. 11, and causes the control unit 101 to display the first rod model LM 1 and the bone model BM (S6). In this process, it is desirable that the operator determines the position of the first rod model LM 1 with respect to the bone model BM such that the first rod model LM 1 is aligned with (parallel to) the surface of the bone model BM as much as possible as shown in FIG. 11, because by doing so it becomes easier to guide the first rod to the feature point when the first rod is inserted into the bone with the bone cutting assist device 1 at a later stage. Therefore, the first rod 31 can be securely supported by the main body 11, so that the first rod 31 can be more accurately guided to the feature point.

Upon receipt of a position information acquisition instruction from the operator in the state of S6, the first rod model position calculation unit 103 acquires coordinate position information of the first rod model LM 1, on the assumption that the position thereof with respect to the bone model BM corresponds to the position of the first rod model LM (S7). Here, causing the control unit 101 to keep the image representing the bone model with the first rod model inserted therein displayed on the screen allows the operator to determine the positions for inserting the second rod models to the bone model avoiding the position where the first rod is inserted.

Figure 12:
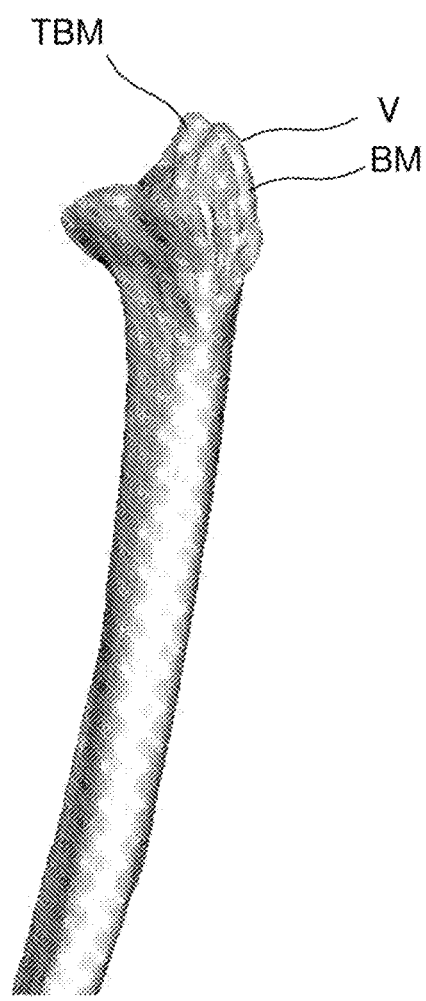
FIG. 12 illustrates an example of the display screen showing respective proximal sides of the bone model and a target bone model superposed on each other.
Figure 13:
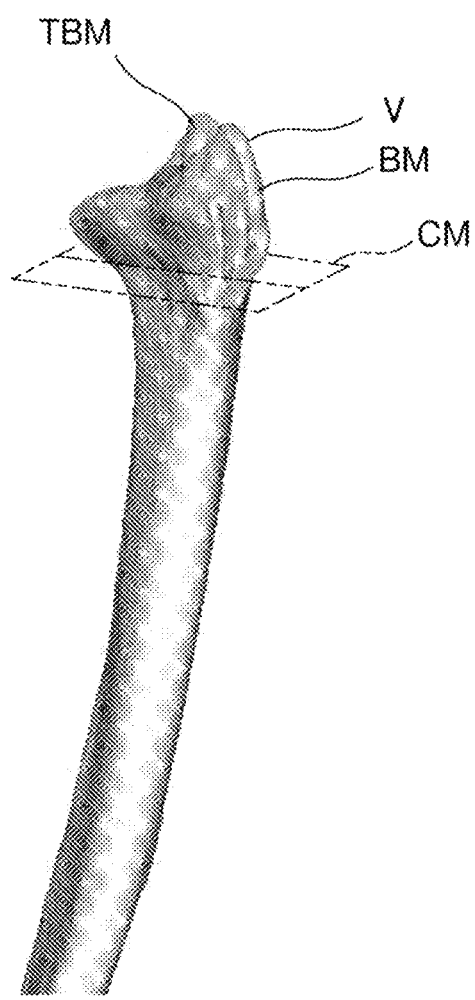
FIG. 13 illustrates an example of the display screen showing an image of a cutting cross-section and the bone model.

The operator then instructs the control unit 101, through the input unit 116, to cause the display unit 114 to display a target bone model TBM (S8). More specifically, the operator causes the control unit 101, through the input unit 116, to display the target bone model TBM such that the respective proximal sides of the bone model BM and the target bone model TBM are superposed on each other, as illustrated in FIG. 12.

Then the control unit 101 causes the display unit 114, according to the instruction from the operator inputted through the input unit 116, to display a plurality of images of the cutting cross-section CM representing the cutting cross-section, in addition to the first rod model LM 1, the bone model BM, and the target bone model TBM (S9). When the operator inputs the position information acquisition instruction by designating, through the input unit 116, one of the cutting cross-section images CM displayed at the desired position with respect to the bone model BM, the bone model generation unit 102 acquires the coordinate position information of the cutting cross-section image CM, on the assumption that the position of the designated cutting cross-section image CM with respect to the bone model BM displayed on the screen (see FIG. 10) corresponds to the position of the cutting cross-section image CM (S10).

The bone piece model generation unit 104 generates divided images of the bone model BM cut at the position corresponding to the cutting cross-section image CM, as bone piece models BPM 1, BPM2 (S11).

Figure 14:
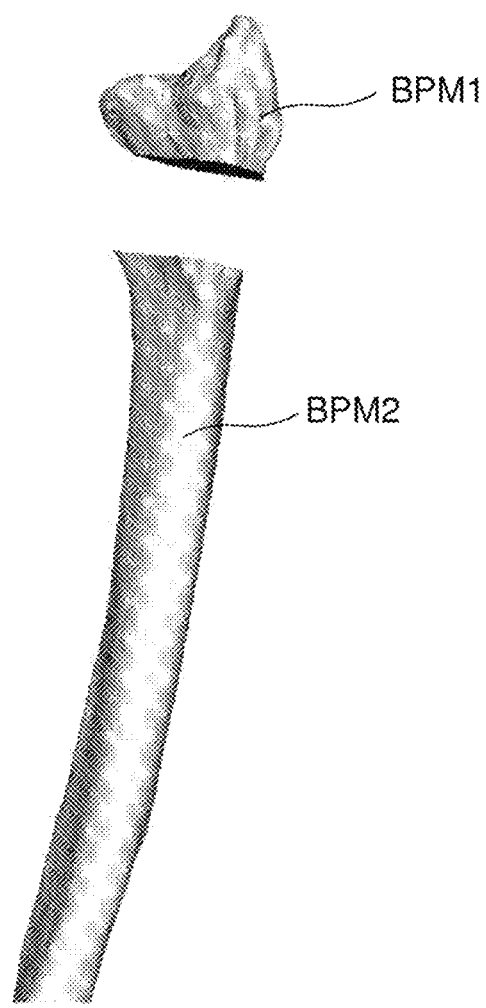
FIG. 14 illustrates an example of the display screen showing bone piece models in place of the bone model.

The control unit 101 further causes the display unit 114 to display the bone piece models BPM 1, BPM2 generated as above, in place of the bone model BM, as shown in FIG. 14 (S12). Although the target bone model TBM is not shown in FIG. 14 and FIG. 15 to be subsequently referred to for the sake of clarity of description, actually the target bone model TBM is displayed, for example by transparent display, such that the visibility of the bone piece models BPM 1, BPM2 to the operator is exempted from being impaired. The control unit 101 causes the bone piece models BPM 1, BPM2 to be displayed in different angles and positions according to the instruction from the operator inputted through the input unit 116. The operator moves the bone piece models BPM 1, BPM2, through the input unit 116, to a position where the difference in shape between a shape formed by combining the bone piece models BPM 1, BPM2 together and the target bone model TBM becomes minimal (S13), and the control unit 101 causes the display unit 114 to display such a state.

Figure 15:
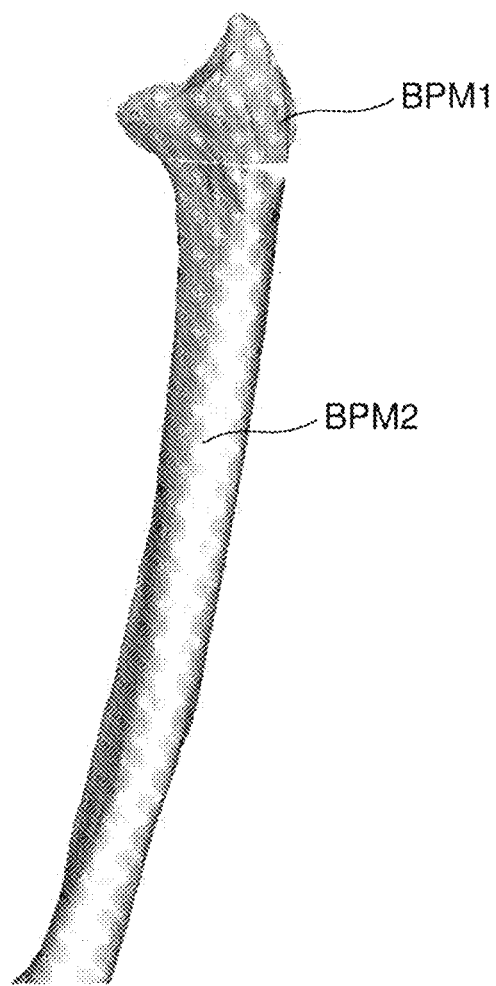
FIG. 15 illustrates an example of the display screen showing the bone piece models combined with each other.

As exemplified in FIG. 15, the operator makes the difference between the shape formed by combining the bone piece models BPM 1, BPM2 together and the target bone model TBM minimal. When the operator inputs the position information acquisition instruction at this point, the bone cutting assist device model generation unit 107 acquires the coordinate position information of each of the bone piece models BPM 1, BPM2, on the assumption that the coordinate positions in the graphic displaying the bone piece models BPM 1, BPM2 at this time point correspond to the target correction positions to which the bone piece models BPM 1, BPM2 are to be respectively moved (S14). Here, the control unit 101 erases the display of the target bone model TBM when the coordinate position information of the bone piece models BPM 1, BPM2 is acquired. However, the foregoing acquisition method of the target correction position is merely exemplary, and any different method may be adopted to acquire the target correction position.

Figure 16:
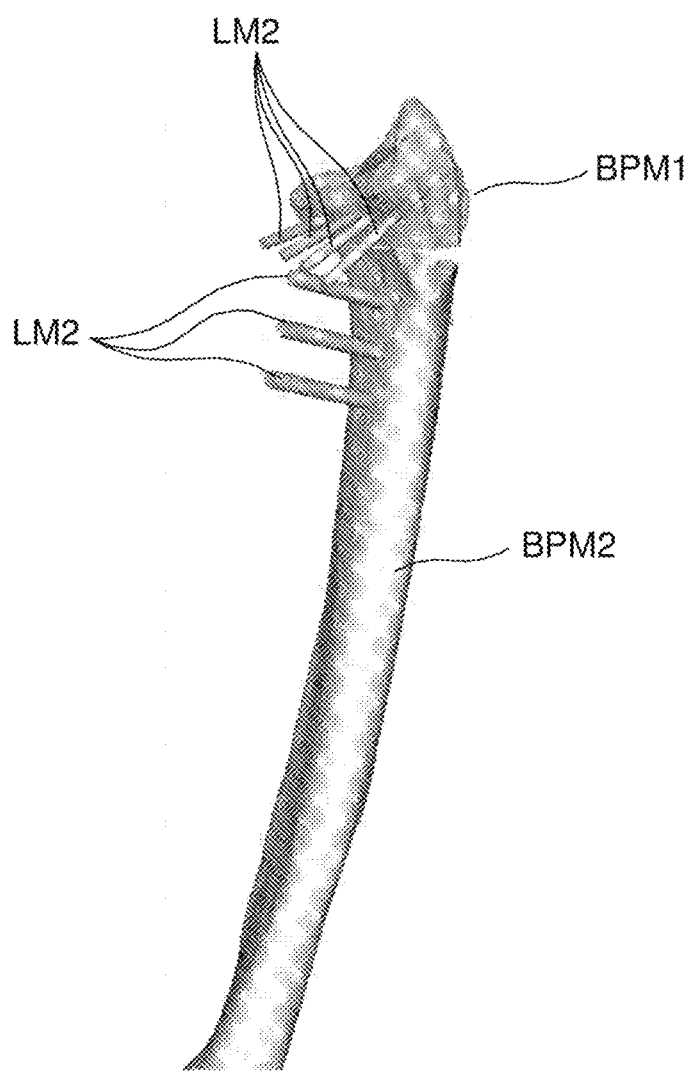
FIG. 16 illustrates an example of the display screen showing second rod models thrust into the bone piece models.

At this point, for example the second rod model position calculation unit 106 causes the display unit 114 to display second rod models LM2, according to the instruction from the operator inputted through the input unit 116 (in this example, four second rod models on the bone piece model BPM 1 and three second rod models on BPM2). The second rod model position calculation unit 106 causes the second rod models LM2 in different positions on the graphic, according to the instruction from the operator. The operator arranges such that, for example, a state where each of the second rod models LM2 is thrust (inserted) into the bone piece model BPM 1 or BPM2 through a desired position is displayed (S15). The control unit 101 keeps the display of the image representing the bone piece model with the second rod models thrust thereto. As exemplified in FIG. 16, an image representing a plurality of second rod models LM2 thrust into each of the bone piece models BPM 1, BPM2 is displayed.

Displaying at this point the bone piece model BPM 1 with the first rod model LM 1 thrust thereto allows the operator to easily avoid the position where the first rod model LM 1 is inserted, when determining the positions on the bone piece models BPM 1, BPM2 where the second rod models LM2 are to be inserted.

Upon receipt of the position information acquisition instruction from the operator when the second rod models LM2 are thrust into each of the bone piece models BPM 1, BPM2, the second rod model position calculation unit 106 acquires the coordinate position information of the second rod models LM2 on the assumption that the coordinate positions of the respective second rod models LM2 shown on the graphic at this point correspond to the positions of the second rod models LM2 with respect to the bone piece models BPM 1, BPM2 located at the target correction position (S16).

The second rod model position calculation unit 106 then calculates the coordinate position information indicating the positions of the second rod models LM2 with respect to the bone piece models BPM 1, BPM2, determined when the bone piece models BPM 1, BPM2 have moved from the target correction position to the position where the bone piece models BPM 1, BPM2 constitute the aforementioned bone model BM (S17).

Here, at S15 the operator may cause one of the second rod models LM2 to be displayed so as to be superposed on the first rod model LM 1 being displayed (S15), to locate the second rod model LM2 at the same position as the first rod model LM 1, to thereby acquire the coordinate position information of the second rod model LM2 (S16). In this case, the position to generate the second guide hole model corresponding to the mentioned second rod model LM2 is regarded as the same position as that of the first guide hole model in the generation process of the second guide hole model (S186) to be subsequently described, and hence the second guide hole model is not generated and instead the first guide hole model is employed as the second guide hole model.

The calculation methods of the first rod model position and the second rod model positions are not limited to the above. For example, the operations of S5 to S7 may be performed after S9 to S16, to calculate the first rod model position after the calculation of the second rod model positions. In this case, the positions of the second rod models LM2 can be easily avoided when determining the position of the first rod model LM 1.

Then the bone cutting assist device model generation unit 107 generates the bone cutting assist device model (S18). The bone cutting assist device model generation unit 107 generates a fitting surface model representing the shape of the fitting surface that fits the surface shape of the bone model BM, utilizing the three-dimensional data of the bone model BM (S182).

The bone cutting assist device model generation unit 107 also generates a main body model including the fitting surface model and corresponding to the main body 11 of the bone cutting assist device 1, according to the instruction from the operator (S183).

Then the bone cutting assist device model generation unit 107 generates a cutting slit model representing the cutting slit having a predetermined thickness, width, and length in the main body model, at the position and angle indicated by the position information of the cutting cross-section acquired at S10 (S184). In this process, the bone cutting assist device model generation unit 107 also generates a support portion having a predetermined thickness, on an outer side of the slit model.

In addition, the bone cutting assist device model generation unit 107 generates, in the main body model, a first guide hole model representing the first guide hole through which the first rod model is to be inserted, utilizing the position information of the first rod model acquired at S7 (S185). More specifically, the bone cutting assist device model generation unit 107 generates the first guide hole model having the same or a slightly larger diameter than the first rod model and a predetermined length, at the position on the main body model indicated by the position information of the first rod model acquired at S7. The bone cutting assist device model generation unit 107 generates the first guide hole model including the hole having the mentioned diameter, with a support portion formed around the hole in a predetermined thickness.

Further, the bone cutting assist device model generation unit 107 generates, in the main body model, second guide hole models representing the second guide holes through which the second rod models are to be inserted, utilizing the position information of the second rod models acquired at S17 (S186). More specifically, the bone cutting assist device model generation unit 107 generates the second guide hole models having the same or a slightly larger diameter than the second rod models and a predetermined length, at the position on the main body model indicated by the position information of the second rod models acquired at S17. The bone cutting assist device model generation unit 107 generates the second guide hole models including the hole having the mentioned diameter, with a support portion formed around the hole in a predetermined thickness.

Through the mentioned process, the bone cutting assist device model generation unit 107 generates the bone cutting assist device model M representing the bone cutting assist device 1 including the main body 11, and the fitting surface 12, the cutting slit 13, the first guide hole 14, and the second guide holes 15 formed in the main body 11, as shown in FIG. 1 and FIG. 2.

Then the block model generation unit 109 generates a block model (S19). The block model generation unit 109 generates a stereographic image model (S191), a fitting surface model to be applied to a corrected bone model RBM, in the same way as S182 and S183 (S192), the fitting surface model having a shape that fits the surface shape of the corrected bone model RBM representing the shape of the bone cutting assist device, which is the correction goal composed of the bone piece models BPM 1, BPM2 located at the target correction position, and a main body model (S193). The main body model is generated at a position to span over bone piece models BPM 1, BPM2 constituting the corrected bone model RBM.

The block model generation unit 109 then generates an insertion hole model in the same way as S186, at the position on the main body model indicated by the position information of the second rod model acquired at S16 (S194). Here, the block model generation unit 109 forms the second guide hole model with a thickness in the longitudinal direction of the second rod that is the same as the thickness of the main body model. The block model generation unit 109 thus generates the block model including the insertion hole model and the fitting surface model.

Then the generation data output unit 108 outputs, according to the instruction from the operator, the three-dimensional manufacturing data representing the bone cutting assist device model generated by the bone cutting assist device model generation unit 107 through process from S181 to S186, for example to a USB memory, another information processing apparatus, or an NC machine tool, through the communication interface 115 (S20). Likewise, the block manufacturing data output unit 120 outputs the three-dimensional manufacturing data representing the block model generated by the block model generation unit 109 through the process from S191 to S194 (S21).

Thereafter, the operator causes the NC machine tool to form the bone cutting assist device 1 and the block 2 shown in FIG. 1 and FIG. 5, or forms the bone cutting assist device 1 and the block 2 through a rapid prototyping method such as optical modelling, utilizing the three-dimensional manufacturing data representing the bone cutting assist device model and the block model outputted as above. Alternatively, the operator may form the bone cutting assist device 1 and the block 2 by a resin molding process using a tooling formed according to the three-dimensional data.

For example, the operator may form the bone cutting assist device 1 and the block 2 by processing a material (e.g., metal, plastic, or ceramic) through a desired molding method such as optical modelling, on the basis of the three-dimensional manufacturing data. The optical modelling refers to a technique of curing a liquid-phase UV-curable resin (liquid that solidifies by reacting to UV light) with UV laser of an optical modelling apparatus and stacking the cured resin, thereby forming a three-dimensional object substantially equal to the 3D data, in a short time.

To be more detailed, for example, data of the three-dimensional model designed by CAD is outputted in an STL format, and the three-dimensional model is sliced in a pitch of 0.05 to 0.25 mm so as to convert into contour data for optical modelling. A semiconductor laser draws a cross-sectional shape on the surface of the resin liquid in a tank according to the contour data, so that the portion irradiated with the laser beam is solidified through chemical reaction. When one layer is formed, the substrate carrying the formed object thereon sinks by an amount corresponding to the slice pitch, and the next cross-sectional portion is formed by laser scanning and stacked. By stacking thus the thin cross-sectional portions continuously, the three-dimensional model is formed under the surface of the liquid, and is then finished through subsequent steps such as cleaning.

Here, it is preferable that the block 2 is formed of a metal, because the block 2 remains inside the patient's body when the diseased part of the patient is closed after the operation.

Through the foregoing method of manufacturing the bone cutting assist device, the custom-made bone cutting assist device 1 and the block 2 that fit the patient and his/her bone can be easily obtained, and optimum gone correction suitable to each of different patients can be performed.

Hereunder, an operation procedure for a bone to be treated utilizing the bone cutting assist device 1 and the block 2 formed as above will be described.

(1) First, the diseased part of the patient is incised so as to expose the portion to be cut of the bone to be treated.

Figure 17:
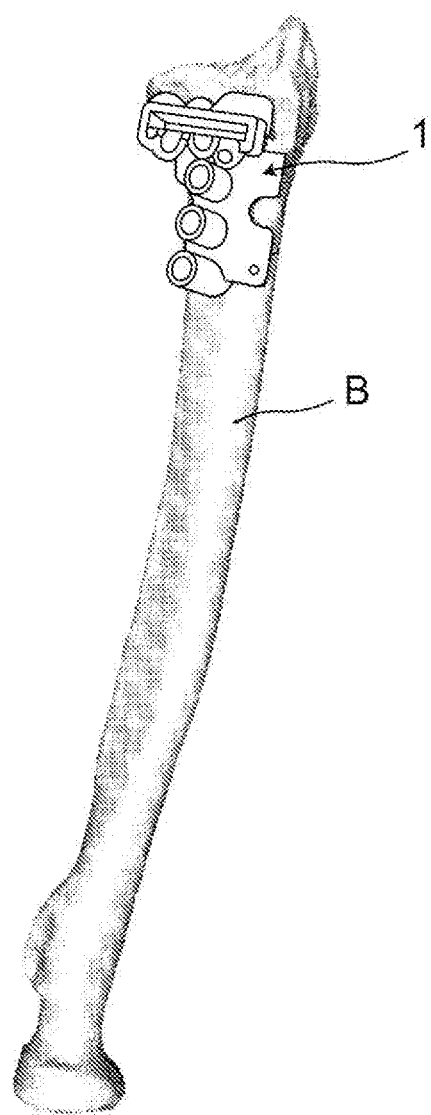
FIG. 17 is a drawing for explaining an operation procedure of a bone to be treated, showing the bone cutting assist device set in close contact with the bone to be treated, with the fitting surface fitted to an appropriate position.

(2) Then the bone cutting assist device 1 is brought into close contact with the bone B to be treated, with the fitting surface 12 fitted to an appropriate position on the surface of the bone B, as shown in FIG. 17. By doing so, the bone cutting assist device 1 is attached to the surface of the bone B to be treated at the target position that matches the cutting cross-section.

Figure 18:
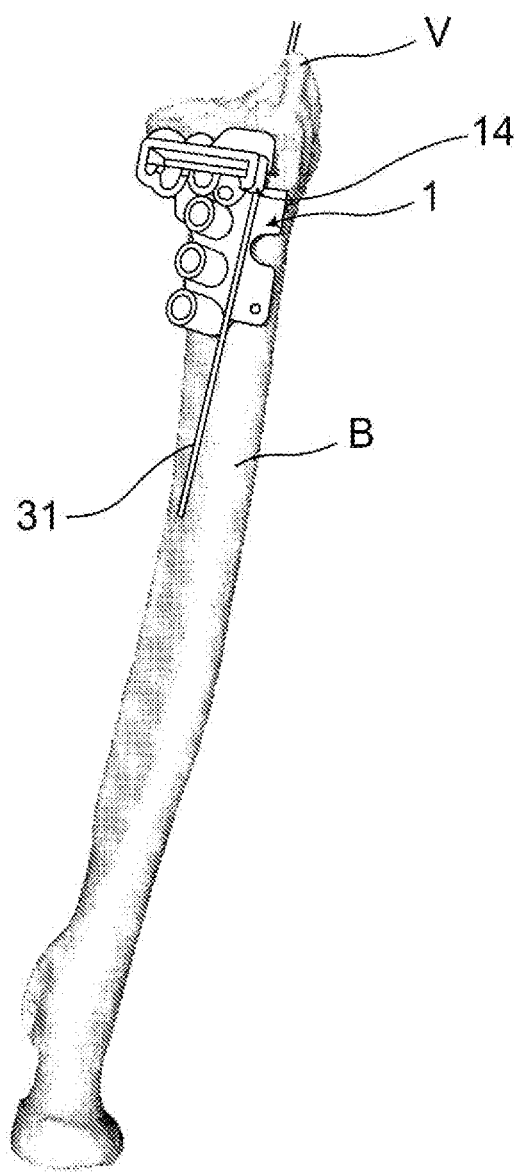
FIG. 18 is a drawing for explaining the operation procedure of the bone to be treated, showing a first rod inserted through a first guide hole of the bone cutting assist device and thrust into the bone to be treated.

(3) The first rod 31 is then inserted through the first guide hole 14 of the bone cutting assist device 1 and inserted into the bone B to be treated, as shown in FIG. 18. The surgeon may, for example, insert the tip portion of an electric drill through the first guide hole 14, to perforate in advance the thrusting hole in the bone cutting assist device 1 for the first rod 31, at the angle and position guided by the first guide hole 14. In addition, the surgeon inserts the first rod 31 into the bone cutting assist device 1, to a sufficient depth to reach the feature point V of the bone B. Here, the first rod 31 is a bar-shaped material with a pointed tip portion, having the same size as the first rod model LM 1.

Whether the first rod 31 is thrust through the feature point V may be either visually confirmed by incising the diseased part until the portion corresponding to the feature point V is exposed, or confirmed with an X-ray image by shooting the portion corresponding to the feature point V with X-ray. The fact that the first rod 31 has reached the feature point V through the first guide hole 14 and the bone B assures that the bone cutting assist device 1 is located at the planned position on the bone B.

Figure 19:
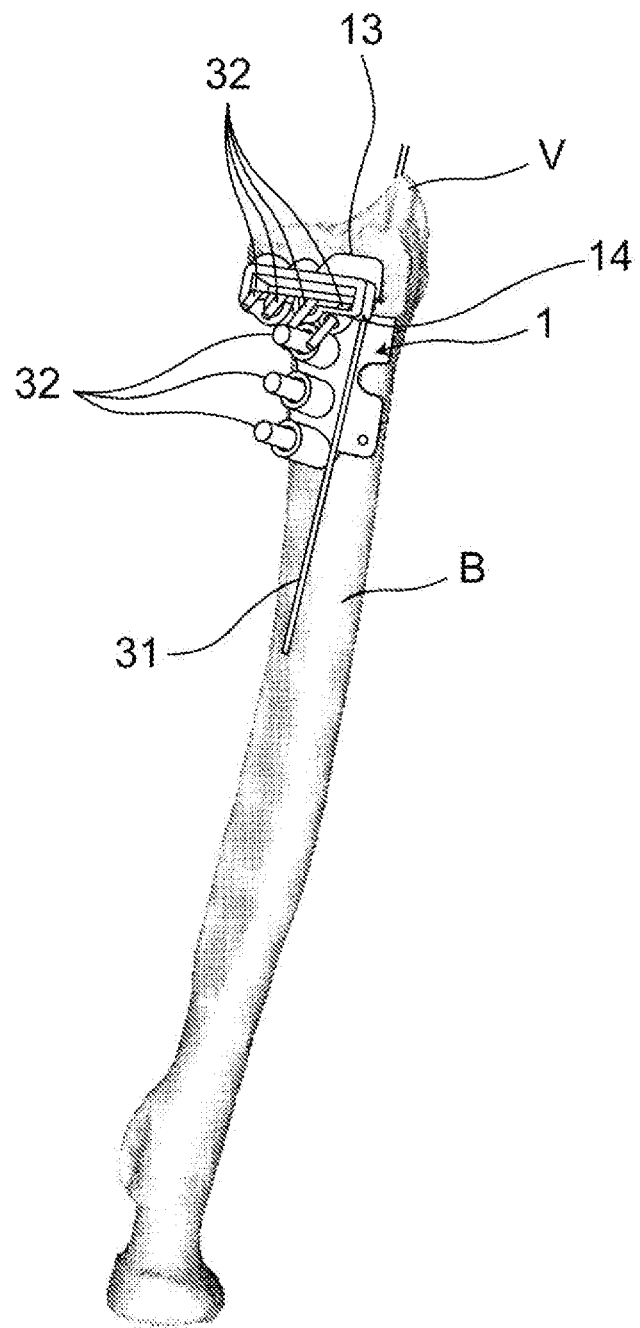
FIG. 19 is a drawing for explaining the operation procedure of the bone to be treated, showing second rods respectively inserted through all second guide holes of the bone cutting assist device and thrust into the bone B to be treated.

(4) Then the second rods 32 are respectively inserted through all the second guide holes 15 of the bone cutting assist device 1 set as above and inserted into the bone B as shown in FIG. 19, in the same way as the insertion and thrusting of the first rod 31. In this process, the surgeon may insert the second rod 32 through the bone cutting assist device 1, to a sufficient depth for fixing the second rod 32 in the bone B. Here, the second rods 32 are formed in the same shape as the first rod 31. In this embodiment, since the second guide holes 15 are provided on each of the bone pieces to be divided thereafter by cutting the bone B to be treated, three second rods 32 are inserted at the positions corresponding to one of the bone pieces produced by cutting the bone B to be treated, and four second rods 32 are inserted at the positions corresponding to the other bone piece.

(5) Then the surgeon inserts a cutting jig such as an electric saw in the cutting slit 13 and activates the cutting jig to thereby cut and divide the bone B. In the case where the first rod 31 is located at a position that interferes with the cutting operation, the first rod 31 is removed from the bone B and the bone cutting assist device 1 before the cutting. In the case where any of the second rods 32 is located at a position that interferes with the cutting operation, such second rod 32 may be removed from the bone B and the bone cutting assist device 1 before the cutting, and the removed second rod 32 may be again inserted in the hole formed in the bone B by the thrusting of (4), after the cutting. Further, in the case where any of the second rods 32 is passed through the cutting cross-section when the cutting is to be performed, such second rod 32 is also cut.

Figure 20:
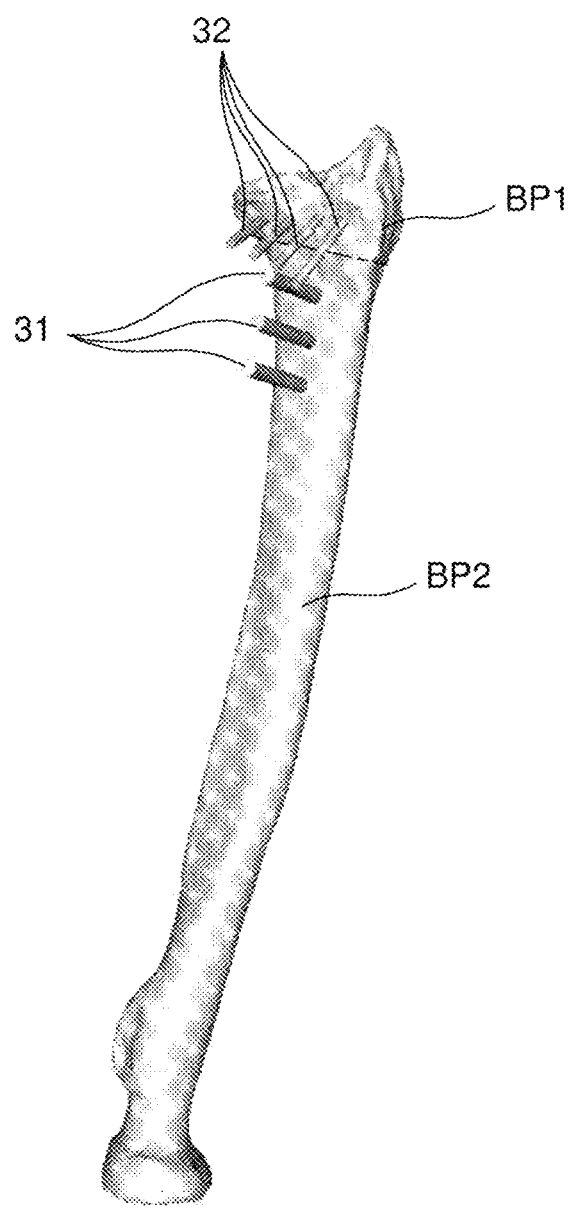
FIG. 20 is a drawing for explaining the operation procedure of the bone to be treated, showing the second rods thrust into the bone pieces.

(6) After the cutting operation, the first rod 31 is removed, and the bone cutting assist device 1 is removed from the bone B leaving the second rods. In this embodiment, at this point the bone B to be treated us divided into the bone pieces BP1, BP2, each of which have the second rod 32 thrust thereto, as shown in FIG. 20. However, in the case where the first guide hole model that also serves as the second guide hole model is formed in the generation process of the bone cutting assist device model of S18 (S186), the surgeon keeps the first rod 31 thrust into the bone B. The first rod 31 is utilized as second rod 32 in the next step (7).

(7) The surgeon then moves the bone pieces BP1, BP2 to the predetermined target correction position by visual measurement (see FIG. 21). Thereafter, the surgeon passes the second rods 32 thrust into the bone pieces BP1, BP2 through the insertion holes 23 of the block 2, and applies the block 2 to the bone pieces BP1, BP2 as shown in FIG. 22. As described above, the insertion holes 23 are formed in the block 2 corresponding to the second rods 32 thrust into the bone pieces BP1, BP2 located at the target correction position. The surgeon readjusts the position of the bone pieces BP1, BP2 so as to enable all of the second rods 32 to be inserted through the corresponding insertion hole 23, after moving the bone pieces BP1, BP2 to the target correction position by visual measurement. When all of the second rods 32 thrust into the bone pieces BP1, BP2 are inserted through the corresponding insertion hole 23, each of the bone pieces BP1, BP2 can be regarded as being accurately located at the target correction position. In other words, the relative positional relationship between the bone pieces BP1, BP2 is corrected to the positional relationship indicated by the target correction position, by inserting the second rods 32 through the respective insertion holes 23 of the block 2.

(8) Finally, the surgeon combines and fixes the bone pieces BP1, BP2 with the block 2, upon locating the bone pieces BP1, BP2 at the target correction position. In the case where a gap is produced between the bone pieces BP1, BP2, a graft is inserted in the gap. The graft can be designed with a computer. The computer-designed graft can be fabricated by processing a material (e.g., metal, plastic, or ceramic) through a desired formation method such as 3D cutting or NC processing. After combining and fixing the bone pieces BP1, BP2, the diseased part of the patient is closed, leaving the block 2 inside the patient's body.

To combine the bone pieces BP1, BP2, any desired method known in the art may be employed. The bone pieces may be combined with an internal fixing material such as a plate, a screw, a wire, or an intramedullary nail, and the gap, which is a defective part of bone, may be filled with calcium phosphate or a grafted bone. To fill the gap, for example, a biocompatible material such as calcium phosphate (e.g., hydroxyapatite), @TCP, or calcium phosphate paste may be employed. Alternatively, bone graft may be adopted for the defective part of bone.

After the bone pieces BP1, BP2 are combined, it is desirable to maintain the combined state for a long period of time. This is because the corrected state is maintained so as to assure the effectiveness of the correction.

With the bone cutting assist device 1 and the block 2 configured as above according to this embodiment, the bone can be cut, in the corrective bone cutting operation, along a proper cutting cross-section calculated in advance through computer simulation, and the bone pieces produced after the cutting can be easily moved to a proper target correction position determined through computer simulation. Therefore, the corrective bone cutting operation can be securely and easily performed, without depending on the experience, proficiency or skill of the surgeon as in conventional operations.

The present invention may be modified in various manners, without limitation to the foregoing embodiment.

Figure 23:
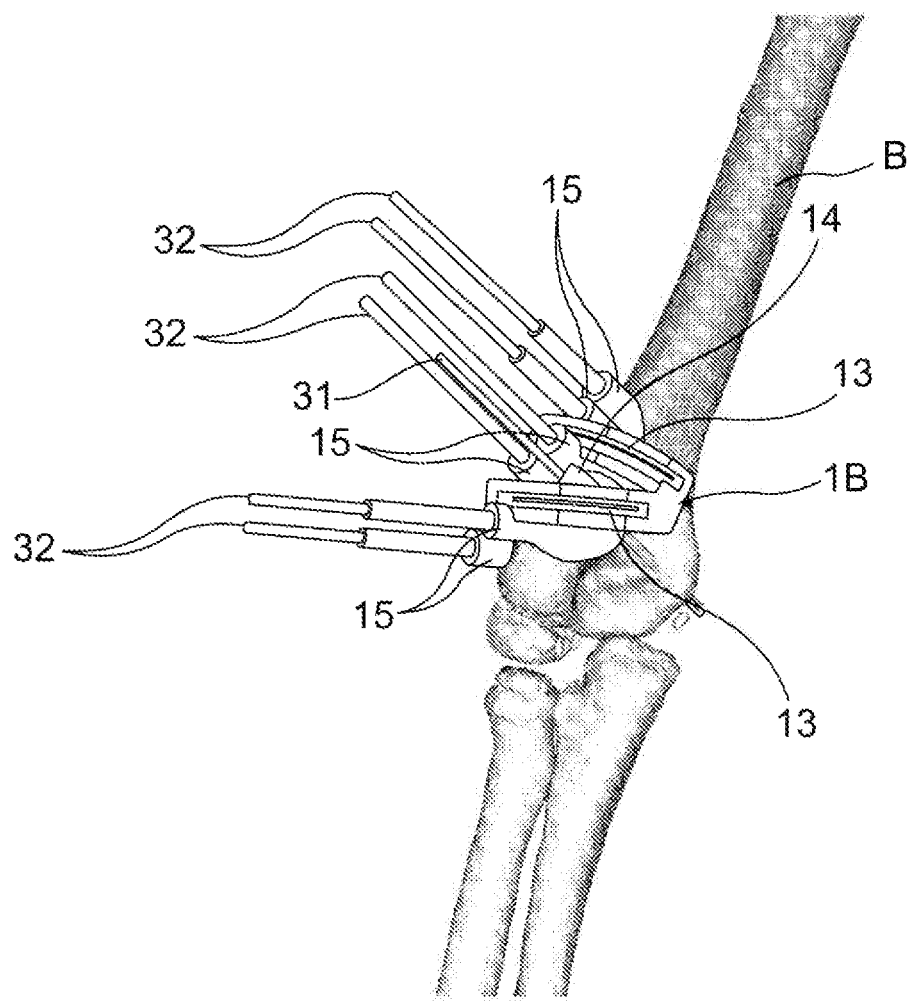
FIG. 23 is a perspective view showing a bone cutting assist device according to another embodiment of the present invention.

For example, although a single cutting slit 13 is formed in the bone cutting assist device 1 in the foregoing embodiment, a plurality of cutting slits 13 may be formed instead of one. In this case, the bone model generation unit 102 forms a plurality of cutting slits 13 at S9 to S10, S18, and S19 described above. For example, a bone cutting assist device 1B including two cutting slits 13 can be obtained as shown in FIG. 23. With the bone cutting assist device 1B thus configured, the bone B can be corrected even in the case where the bone B is divided into three or more pieces, or partially resected. In addition, the bone cutting assist device 1B includes the second guide holes 15 that correspond to all of the plurality of bone pieces divided by the cutting, so as to allow the second rods 32 to be thrust into all of such bone pieces. In this case, the position information of a plurality of second rod models is acquired at S15 to S17, and the bone model generation unit 102 generates a plurality of second guide hole models at S18 and S19.

Figure 24:
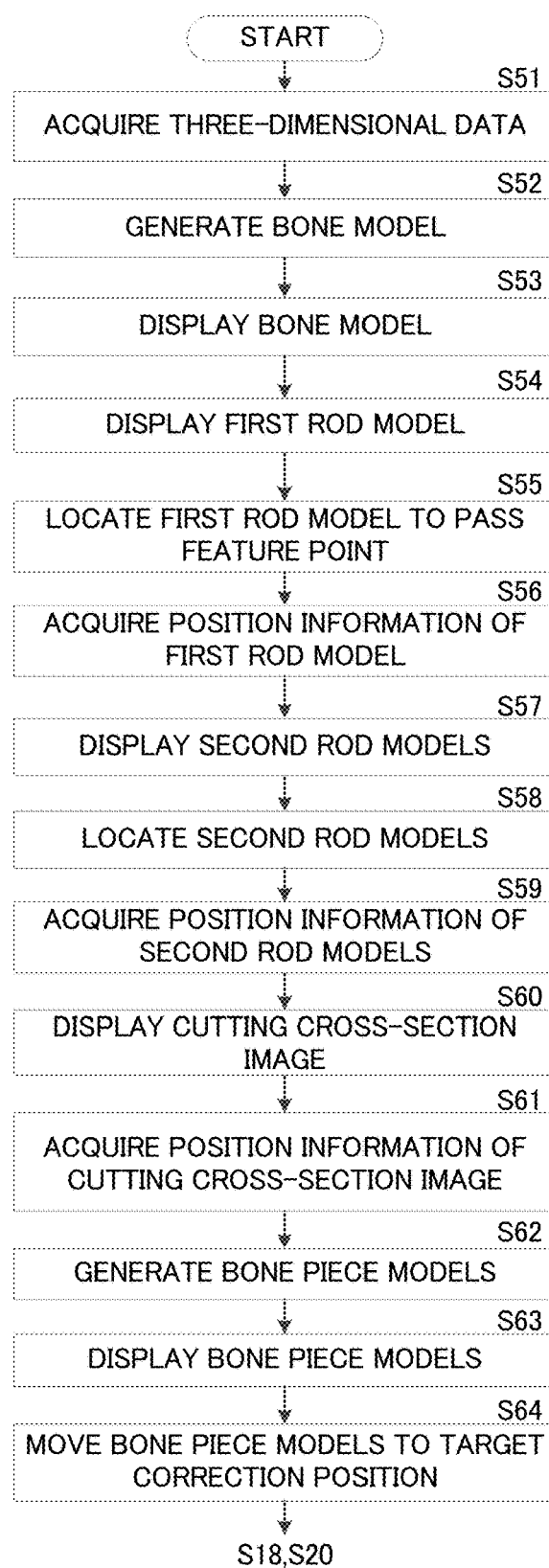
FIG. 24 is a flowchart showing another process performed by the information processing apparatus with the manufacturing program of the bone cutting assist device installed therein, to generate manufacturing data of the bone cutting assist device.

Alternatively, the bone cutting assist device 1 may be configured as follows. FIG. 24 is a flowchart showing another process performed by the information processing apparatus 10 with the manufacturing program of the bone cutting assist device installed therein, to generate the manufacturing data of the bone cutting assist device. The description of the same processes as those described with reference to FIG. 8 will not be repeated.

The information processing apparatus 10 performs, in the same way as the process described with reference to FIG. 8, the acquisition of the three-dimensional data (S51), the generation of the bone model BM (S52), the display of the bone model BM on the display unit 114 (S53), and the display of the first rod model LM 1 (S54).

The control unit 101 then displays the first rod model LM 1 at different positions according to the instruction from the operator inputted through the input unit 116. The operator causes, through the input unit 116, the first rod model LM 1 to be thrust into the bone model BM through a desired position in the bone model BM, for example the feature point V showing a shape that the operator can visually recognize easily in the shape of the bone model BM as shown in FIG. 11, and causes the control unit 101 to display the first rod model LM 1 and the bone model BM (S55). Upon receipt of the position information acquisition instruction from the operator in the state of S55, the first rod model position calculation unit 103 acquires coordinate position information of the first rod model LM 1, on the assumption that the position thereof with respect to the bone model BM corresponds to the position of the first rod model LM (S56).

Then the control unit 101 causes the display unit 114 to display the second rod models LM2 (S57), and causes the first rod model LM 1 to be displayed at different positions according to the instruction from the operator inputted through the input unit 116. The operator causes, through the input unit 116, the second rod models LM2 to be thrust into the bone model BM through the desired position in the bone model BM, and causes the control unit 101 to display the second rod models LM 2 and the bone model BM (S58). Upon receipt of the position information acquisition instruction from the operator in the state of S58, the second rod model position calculation unit 106 acquires the coordinate position information of the second rod models LM2, on the assumption that the position thereof with respect to the bone model BM corresponds to the position of the second rod models LM2 (S59).

When the operator designates the cutting cross-section by inputting the instruction through the input unit 116 (S60, S61), the bone piece model generation unit 104 generates the bone piece models BPM 1, BPM2 (S62), and the control unit 101 causes the display unit 114 to display the bone piece models BPM 1, BPM2 (S63).

The control unit 101 causes the bone piece models BPM 1, BPM2 to be displayed in different angles and positions according to the instruction from the operator inputted through the input unit 116 (S64). Accordingly, the operator can simulate at S64 whether the bone piece models BPM 1, BPM2 produced upon being cut along the cutting cross-section can be moved to the position that the operator regards as the target correction position. Then the same process as S18 and S20 shown in FIG. 8 is performed, so that the bone cutting assist device 1 is manufactured utilizing the outputted three-dimensional data for manufacturing the bone cutting assist device.

Through the mentioned process, the bone cutting assist device 1, configured to cut and divide the bone deformed into an abnormal condition and correct the bone to the normal positional relationship by changing the positional relationship between the divided bone pieces, can be obtained, the bone cutting assist device 1 including the cutting slit 13, the first guide hole 14, and the second guide holes 15.

Hereunder, an operation procedure for a bone to be treated utilizing the bone cutting assist device 1 formed as above will be described. The description of the same processes as those of the foregoing operation will not be repeated.

(1) First, the diseased part of the patient is incised so as to expose the portion to be cut of the bone to be treated.

(2) Then the bone cutting assist device 1 is brought into close contact with the surface of the bone B to be treated.

(3) The first rod 31 is inserted through the first guide hole 14 of the bone cutting assist device 1 attached as above, and inserted into the bone B to be treated.

(4) Then the second rods 32 are respectively inserted through all the second guide holes 15 of the bone cutting assist device 1 set as above, and inserted into the bone B.

(5) The surgeon then inserts a cutting jig such as an electric saw in the cutting slit 13 and activates the cutting jig to thereby cut and divide the bone B.

(6) After the cutting operation, the operator moves the bone pieces BP1, BP2 to the position regarded as the target correction position.

The bone cutting assist device 1 configured as above can be located at an accurate position with respect to the bone B to be treated, by thrusting the first rod 31 into the bone B to be treated through the first guide hole 14, and securely fixed to the bone B to be treated by thrusting the second rods 32 into the bone B to be treated through the second guide holes 15. Therefore, the bone B to be treated can be cut along an accurately defined cutting cross-section.

The configurations and operations described in the foregoing embodiments with reference to FIG. 1 through FIG. 24 are merely exemplary, and the configurations and operations of the present invention are in no way limited to the above.

Although the bone of the limb is taken up as object of the treatment in the foregoing embodiments, the present invention is applicable to any chose bone without limitation to the limb bone. In the case of a human body, all of the approximately 200 pieces of bones in the human body can be the object of the present invention, including, but not limited to, long bones (e.g., limb bones), short bones, flat bones (e.g., sternum, rib, scapula, ilium), sesamoid bones (e.g., patella), and irregular bones (e.g., facial skeleton, vertebra). However, the long bones (e.g., limb bones) are appropriate for correction by the method according to the present invention. The present invention is typically applicable to malunited bones.

The bone cutting assist device manufacturing program may be provided to the user in a desired format. For example, the program may be distributed to the users in a form of a recording medium having the program recorded thereon, or by allowing the users to download the program to the user's terminal device through a network. The bone cutting assist device manufacturing program may be provided either for a fee or free of charge. Examples of the recording medium on which the program may be recorded include a flexible disk, an MO disk, a DVD, or any other desired recording medium. In addition, any desired network, including the internet, may be employed.

In the present description, the three-dimensional display is normally realized through an orthogonal system, however any desired system may be employed provided that a three-dimensional image can be displayed.

In the present description, the term "bone" refers to the support organ of a spinal animal including the individual elements of the endoskeleton. The bones of the spinal animal are primarily constituted of bone tissue, except for cyclostomes and cartilaginous fishes. The present description is also applicable to a cartilage. In the present description, when a hard connective tissue constituting the majority of the skeleton of the spinal animal is specifically referred to, the term "hard bone" is employed. It may also be understood that, although the bone is taken up as object of the present description, the method and the device of the present invention are equally applicable to other parts of the body than the bones.

In the present description, the parameters in the three-dimensional direction with respect to the bone are elements that indicate each dimension in the three-dimensional display employed, for example the elements (for example, vectors) with respect to x-, y-, and z-axes when the space is expressed on the basis of the orthogonal system. The space defined by the x-, y-, and z-axes can be substitutionally expressed by a rotation axis or a rotation angle.

In the present description, the "treatment" of the bone refers to applying a physical effect to the bone, including, but not limited to, rotation, excision, cutting, graft insertion, extension, and fixing.

In the present description, the term "patient" refers to a subject, to whom/which the treatment according to the embodiments may be applied. Preferably, the patient or subject may be a human.

In the present description, the "cutting" of the bone refers to dividing a bone into two or more parts. The cutting of the bone is typically performed with a bone cutting device such as a bone saw. In the present description, a part where the bone is cut may also be referred to as "osteotomy section".

In the present description, "fixing" a bone (bone piece) refers to substantially maintaining, after a treatment is performed, the condition obtained through the treatment. Generally, the fixing of the bone is performed with the treated bone alone.

The invention claimed is:

1. A method of manufacturing a bone cutting assist device used for cutting a bone deformed into an abnormal condition, the method comprising:
   acquiring three-dimensional data of a bone to be treated and generating a three-dimensional bone model representing the bone to be treated, on a basis of the acquired three-dimensional data:
   generating bone piece models divided by cutting the bone model along a cutting cross-section for correction defined with respect to the bone model, the bone piece models being movable or rotatable to a target correction position approximate to a target bone model representing a correction goal of the bone to be treated;
   determining a feature point that is a part on the bone model where a first rod model representing a shape of a first rod to be used for securing that the bone cutting assist device is located at a planned position on the bone to be treated in reference to the feature point is virtually thrust into, the feature point being a position on the bone, the position being where, by the first rod is allowed to pass through the bone cutting assist device and to be thrust into the bone, the bone cutting assist device is to be arranged at the planned position on the bone to be treated;

calculating a position of the first rod model, the first rod model being virtually attached to the feature point determined at the determining;

calculating, on a basis of a position of a second rod model attached to each of the bone piece models assumed to be located at the target correction position, a position of the second rod model on an assumption that the bone piece models are located at a position corresponding to the bone model;

generating a bone cutting assist device model representing a bone cutting assist device including a fitting surface to be fitted to a surface of the bone model, a cutting slit formed at a position corresponding to the cutting cross-section, to guide a cutting jig toward the cutting cross-section, a first guide hole formed at the calculated position of the first rod model, so as to allow the first rod model to be virtually inserted, and a second guide hole formed at the calculated position of the second rod model, so as to allow the second rod model to be virtually inserted;

outputting three-dimensional manufacturing data representing the generated bone cutting assist device model; and manufacturing the bone cutting assist device according to the outputted three-dimensional manufacturing data, the first guide hole extending in a first direction, and the second guide hole extending in a second direction being different from the first direction.

2. The method of manufacturing a bone cutting assist device according to claim 1, further comprising:

generating a block model representing a block including insertion holes for inserting the second rod models, the insertion holes each being formed at a position corresponding to the second rod model attached to one of the bone piece models located at the target correction position;

outputting three-dimensional data for manufacturing the block, the data representing the block model generated in the generating of the block model; and manufacturing the block according to the outputted three-dimensional data for manufacturing the block.

3. The method of manufacturing a bone cutting assist device according to claim 2, wherein the generating of the block model includes generating a block model representing a block including insertion holes for respectively inserting the first and second rod models, the insertion holes being located at positions corresponding to the first rod model and the second rod models attached to the bone piece models located at the target correction position, the outputting of the block manufacturing data includes outputting three-dimensional data for manufacturing the block representing the block model generated in the generating of the block model, and the manufacturing of the block includes manufacturing the block according to the three-dimensional data for manufacturing the block outputted in the outputting of the block manufacturing data.

4. The method of manufacturing a bone cutting assist device according to claim 1, wherein the feature point shows an anatomical landmark indicating a shaped part representing a feature of a bone type where the bone to be treated belongs.

5. The method of manufacturing a bone cutting assist device according to claim 1, wherein the feature point is a protruding part as an anatomical landmark at an end of the bone model.

6. A non-transitory computer-readable recording medium having a program for manufacturing a bone cutting assist device recorded thereon, wherein the program for manufacturing a bone cutting assist device causes a computer to act as:

a bone model generation unit that acquires three-dimensional data of a bone to be treated and generates a three-dimensional bone model representing the bone to be treated, on a basis of the acquired three-dimensional data;

a bone piece model generation unit that generates bone piece models divided by cutting the bone model along a cutting cross-section for correction defined with respect to the bone model, the bone piece models being movable or rotatable to a target correction position approximate to a target bone model representing a correction goal of the bone to be treated;

a first rod model position calculation unit that calculates a position of a first rod model attached to a feature point that is a part on the bone model where the first rod model representing a shape of a first rod to be used for securing that the bone cutting assist device is located at a planned position on the bone to be treated in reference to the feature point is virtually thrust into, the feature point being determined as a position on the bone, the position being where, by the first rod is allowed to pass through the bone cutting assist device and to be thrust into the bone, the bone cutting assist device is to be arranged at the planned position on the bone to be treated;

a second rod model position calculation unit that calculates, on a basis of a position of a second rod model attached to each of the bone piece models assumed to be located at the target correction position, a position of the second rod model on an assumption that the bone piece models are located at a position corresponding to the bone model;

a bone cutting assist device model generation unit that generates a bone cutting assist device model representing a bone cutting assist device including a fitting surface to be fitted to a surface of the bone model, a cutting slit formed at a position corresponding to the cutting cross-section, to guide a cutting jig toward the cutting cross-section, a first guide hole formed at the calculated position of the first rod model, so as to allow the first rod model to be virtually inserted, and a second guide hole formed at the calculated position of the second rod model, so as to allow the second rod model to be virtually inserted; and a manufacturing data output unit that outputs three-dimensional manufacturing data representing the generated bone cutting assist device model, the program further causes the computer to act so that:

the first guide hole extends in a first direction; and the second guide hole extends in a second direction being different from the first direction.

7. The non-transitory computer-readable recording medium according to claim 6, having the program for manufacturing a bone cutting assist device recorded thereon, wherein the program for manufacturing a bone cutting assist device causes the computer to further act as:
a block model generation unit that generates a block model representing a block including insertion holes for inserting the second rod models, the insertion holes each being formed at a position corresponding to the second rod model attached to one of the bone piece models located at the target correction position;
a block manufacturing data output unit that outputs three-dimensional data for manufacturing the block, the data representing the block model generated by the block model generation unit.

8. The non-transitory computer-readable recording medium according to claim 7, having the program for manufacturing a bone cutting assist device recorded thereon,
wherein the program for manufacturing a bone cutting assist device causes the computer to further act such that:
the block model generation unit generates a block model representing a block including insertion holes for respectively inserting the first and second rod models, the insertion holes being located at positions corresponding to the first rod model and the second rod models attached to the bone piece models located at the target correction position, and
the block manufacturing data output unit outputs three-dimensional data for manufacturing the block representing the block model generated by the block model generation unit.

9. The non-transitory computer-readable recording medium according to claim 6, having the program for manufacturing a bone cutting assist device recorded thereon,
wherein the feature point shows an anatomical landmark indicating a shaped part representing a feature of a bone type where the bone to be treated belongs.

10. A bone cutting assist device used for cutting and dividing a bone deformed into an abnormal condition, the bone cutting assist device comprising:
a cutting slit formed at a position corresponding to a cutting cross-section along which the bone is to be cut, and configured to guide a cutting jig toward the cutting cross-section when the bone cutting assist device is in contact with a surface of the bone;
a first guide hole that guides a first rod to a feature point that is a part on the bone model where a first rod to be used for securing that the bone cutting assist device is located at a planned position on the bone to be treated in reference to the feature point is virtually thrust into, the feature point being determined as a position on the bone, the position being where, by the first rod is allowed to pass through the bone cutting assist device and to be thrust into the bone, the bone cutting assist device is to be arranged at the planned position on the bone to be treated; and
at least one second guide hole that guides a second rod to be inserted into the bone to the bone, when the bone cutting assist device is in contact with the surface of the bone,
wherein the first guide hole extending in a first direction, and
the second guide hole extending in a second direction being different from the first direction.

11. The bone cutting assist device according to claim 10, further comprising:
a fitting surface formed at a position to oppose the bone to be corrected, so as to fit to a surface of the bone;
wherein the cutting slit is formed at a position corresponding to the cutting cross-section, when the fitting surface is fitted to the surface of the bone,
the first guide hole guides the first rod to the feature point when the fitting surface is fitted to the surface of the bone; and
the second guide holes guide, when the fitting surface is fitted to the surface of the bone, the second rods to be inserted into the bone, such that the second rods thrust into the bone pieces assume a predetermined positional relationship therebetween, after the bone pieces divided along the cutting cross-section are corrected to a positional relationship in a normal condition.

12. The bone cutting assist device according to claim 10, wherein the feature point shows an anatomical landmark indicating a shaped part representing a feature of a bone type where the bone to be treated belongs.

* * * * *

UNITED STATES PATENT AND TRADEMARK OFFICE
CERTIFICATE OF CORRECTION

PATENT NO. : 10,398,510 B2  Page 1 of 1
APPLICATION NO. : 15/035915
DATED : September 3, 2019
INVENTOR(S) : Makoto Goto et al.

It is certified that error appears in the above-identified patent and that said Letters Patent is hereby corrected as shown below:

On the Title Page

Item (72) Inventor should read: Makoto GOTO, Nishinomiya (JP);
Tsuyoshi MURASE, Toyonaka (JP)

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*